(12) United States Patent
Daniloff et al.

(10) Patent No.: US 8,784,893 B2
(45) Date of Patent: Jul. 22, 2014

(54) POLYMER FORMULATIONS FOR DELIVERY OF BIOACTIVE AGENTS

(75) Inventors: George Daniloff, Los Altos, CA (US); David Gravett, Mountain View, CA (US); Robert C. Spiro, Half Moon Bay, CA (US)

(73) Assignee: Carbylan Therapeutics, Inc., Palo Alto, CA (US)

( * ) Notice: Subject to any disclaimer, the term of this patent is extended or adjusted under 35 U.S.C. 154(b) by 1239 days.

(21) Appl. No.: 12/526,027

(22) PCT Filed: Feb. 5, 2008

(86) PCT No.: PCT/US2008/053108
§ 371 (c)(1),
(2), (4) Date: Oct. 18, 2010

(87) PCT Pub. No.: WO2008/098019
PCT Pub. Date: Aug. 14, 2008

(65) Prior Publication Data
US 2011/0033540 A1 Feb. 10, 2011

Related U.S. Application Data

(60) Provisional application No. 60/888,251, filed on Feb. 5, 2007.

(51) Int. Cl.
| | | |
|---|---|---|
| *A61K 31/58* | (2006.01) | |
| *A61K 31/715* | (2006.01) | |
| *A61K 9/00* | (2006.01) | |
| *A61L 27/52* | (2006.01) | |
| *A61K 9/19* | (2006.01) | |
| *A61L 27/20* | (2006.01) | |
| *A61K 47/36* | (2006.01) | |

(52) U.S. Cl.
CPC .............. *A61K 9/0024* (2013.01); *A61L 27/52* (2013.01); *A61K 9/19* (2013.01); *A61L 27/20* (2013.01); *A61K 47/36* (2013.01)
USPC .............. 424/488; 424/489; 514/174; 514/54

(58) Field of Classification Search
CPC .......... A61L 27/20; C08L 5/08; A61K 47/36; A61K 9/0024; A61K 9/146
USPC ............................. 424/488, 489; 514/174, 54
See application file for complete search history.

(56) References Cited

U.S. PATENT DOCUMENTS

| | | | |
|---|---|---|---|
| 2002/0128512 A1 | 9/2002 | Bulpitt et al. | |
| 2005/0176620 A1 | 8/2005 | Prestwich et al. | |
| 2005/0256081 A1* | 11/2005 | Peyman | 514/56 |
| 2006/0141049 A1* | 6/2006 | Lyons et al. | 424/489 |

FOREIGN PATENT DOCUMENTS

| | | |
|---|---|---|
| WO | WO 2005/056608 A | 6/2005 |
| WO | WO 2008/098019 A3 | 8/2008 |

OTHER PUBLICATIONS

Ji (Biomaterials, 27, Published Mar. 23, 2006, pp. 3782-3792).*
Ghosh et al. (Tissue Engineering, vol. 12, No. 3, Published 2006, pp. 601-613).*
Cai, et al., "Injectable glycosaminoglycan hydrogels for controlled release of human basic fibroblast growth factor", Biomaterials, vol. 26, No. 30, pp. 6054-6067 (2005).
Ghosh, et al., "Rheological characterization of in situ cross-linkable hyaluronan hydrogels", Biomacromolecules, vol. 6, No, 5, pp. 2857-2865 (2005).
International Search Report from PCT Patent Application No. PCT/US2008/053108 Mailed Mar. 2, 2009, Published as International Publication No. WO 2008/098019 A3 on Aug. 14, 2008.
Li, et al., "Synthesis and biological evaluation of a cross-linked hyaluronan-mitomycin C hydrogel", Biomacromolecules. vol. 5, No. 3, pp. 895-902 (2004).
Liu, et al., "Accelerated repair of cortical bone defects using a synthetic extracellular matrix to deliver human demineralized bone matrix", J. Ortho. Res., vol. 24, No. 7, pp. 1454-1462 (2006).
Prestwich, et al., "Injectible synthetic extracellular matrices for tissue engineering and repair", Adv, Exp. Med. Biol., vol. 585, pp. 125-133 (2006).
Shu, et al., "Disulfide cross-linked hyaluronan hydrogels", Biomacromolecules, vol. 3, No. 6, pp. 1304-1311 (2002).
Shu, et al., "In-situ crosslinkable hyaluronan hydrogels for tissue engineering", Biomaterials, vol. 25, No. 7-8, pp. 1339-1348 (2004).
Aragona et al., "Long term treatment with sodium hyaluronate-containing artificial tears reduces ocular surface damage in patients with dry eye", Br. J. Opthalmol., vol. 86, pp. 181-184 (2002).

* cited by examiner

*Primary Examiner* — Richard Schnizer
*Assistant Examiner* — Alma Pipic
(74) *Attorney, Agent, or Firm* — Susan T. Evans; McDermott Will & Emery LLP

(57) ABSTRACT

Disclosed in the present application are compositions comprising a bioresorbable polymer matrix and a bio active agent, wherein the bioactive agent is dispersed within polymer matrix as a solid. Also provided herein are methods for preparing a bioactive agent formulation, wherein the agent is present in a solid form and, wherein the agent is occluded into a polymeric matrix by polymerization of polymer matrix precursors or by self assembly of the polymer.

19 Claims, 6 Drawing Sheets

POLYMER FORMULATIONS FOR DELIVERY OF BIOACTIVE AGENTS

This application is a U.S. National Stage of International Patent Application No. PCT/US2008/053108, filed Feb. 5, 2008, which claims the benefit of priority to U.S. Provisional Application No. 60/888,251, filed Feb. 5, 2007, the contents of all of which are hereby incorporated by reference in their entireties.

FIELD OF THE INVENTION

The present invention relates to methods and pharmaceutical compositions comprising a polymer and a biologically active agent in a solid form for the administration and delivery of the biologically active agent. These compositions are useful as pharmaceutical agents. More particularly, the present application relates to polymer compositions comprising solid hydrophobic biologically active agents.

BACKGROUND OF THE INVENTION

Available vehicles for the administration of hydrophobic drugs, such as water-insoluble or low water soluble compounds often result in undesirable side-effects. Such undesired side-effects include hemolysis, thrombophlebitis or at times, blood coagulation. Liposomes and oil-in-water emulsions have been employed as potential carriers for these hydrophobic drugs that may reduce such undesirable side-effects. However, there remain significant problems associated with stability and drug loading capacity associated with the use of these delivery systems.

Implantable medical devices or compositions for the delivery of biologically active agents are known in the art. However, the placement of metal or polymeric devices in the body are useful for treating a variety of medical conditions, but often results in complications. These complications may include increased risk of infection, inflammation, fibrous encapsulation, and potentially a wound healing response resulting in hyperplasia and restenosis.

One approach to reducing these adverse affects is to provide biocompatible implantable devices. Several implantable medical devices capable of delivering biologically active agents through releasing coatings are known in the art, including U.S. Pat. No. 4,916,193; U.S. Pat. No. 4,994,071; U.S. Pat. No. 5,221,698 and U.S. Pat. No. 5,304,121. U.S. Pat. No. 4,970,298 describes a biodegradable collagen matrix suitable for use as a wound implant. The matrix is formed by freeze drying an aqueous dispersion containing collagen, cross-linking the collagen via two cross-linking steps and freeze-drying the cross-linked matrix. The matrix may also contain hyaluronic acid and fibronectin.

EP-A-0274898 describes an absorbable implant material having an open cell, foam-like structure and formed from resorbable polyesters, such as poly-p-dioxanone, other polyhydroxycarboxylic acids, polylactides or polyglycolides. JP-A-03023864 describes a wound implant material comprising a collagen sponge matrix reinforced with fibers of poly-L-lactic acid. The collagen sponge matrix is formed by freeze drying a solution of porcine atherocollagen. EP-A-0562862 describes bioabsorbable wound implant materials that are composites comprising a collagen sponge matrix having embedded therein oriented substructures of solid collagen fibers, films or flakes. The substructures reinforce the collagen sponge and also provide a scaffold for directional cellular migration into the implant.

It is well known that the water insolubility of a number of important drugs, such as amphotericin B, phenyloin, miconazole, cyclosporin, diazepam and etoposide, makes their formulation for administration, such as by intravenous application, particularly difficult. These drugs, for example, are currently marketed in cosolvent systems such as polyethylene glycol or propylene glycol-ethanol-benzyl alcohol mixtures. However severe toxicity problems, such as thrombophlebitis, have been observed with injectable formulations of drugs dissolved in cosolvents. Alternatives to cosolvent systems are micellar solutions or emulsions; however, the presence of toxic surfactants in those systems makes them undesirable for intravenous administration. Many pharmaceutically useful compounds have limited solubility in physiological fluids. Delivery of such compounds presents a formulation challenge and often requires use of hydrophobic carriers which often present undesirable side effects when introduced in contact with the body. In addition, it is also difficult to modulate the pharmacodynamic and pharmacokinetic characteristics of such formulations in vivo. Therefore a continuing need exists for novel, stable and nontoxic formulations and compositions for the delivery of hydrophobic drugs.

The present application describes a composition that utilizes a biocompatible matrix (hydrophilic or hydrophobic) containing a solid form of bioactive agent dispersed in it. Depending on the size (surface) of the bioactive agent particles and the nature of the polymeric matrix (i.e. hydrogel, elastomer, solid polymer, hydratable dry polymer, and biodegradation properties) the rate of said bioactive agent release and duration of the release in vivo may be modulated in much wider range than currently know in the art. In one aspect, the formulations described in this application enable new safer therapeutic products for clinical use.

SUMMARY OF THE INVENTION

The application provides a novel composition of matter comprising a solid form(s) of a bioactive agent(s) and a biocompatible polymer matrix. In one embodiment, there is provided a biocompatible polymer matrix that may be used as an implantable device, wherein the device comprises polymer materials having inherent properties or biological activity that be enhanced when employed in conjunction with the biologically active agent. In certain aspect of the composition, the biological activity resulting from the combination of the biocompatible polymer matrix is synergistic with the biological active agent.

EMBODIMENTS, ASPECTS AND VARIATIONS OF THE INVENTION

Figure 1:
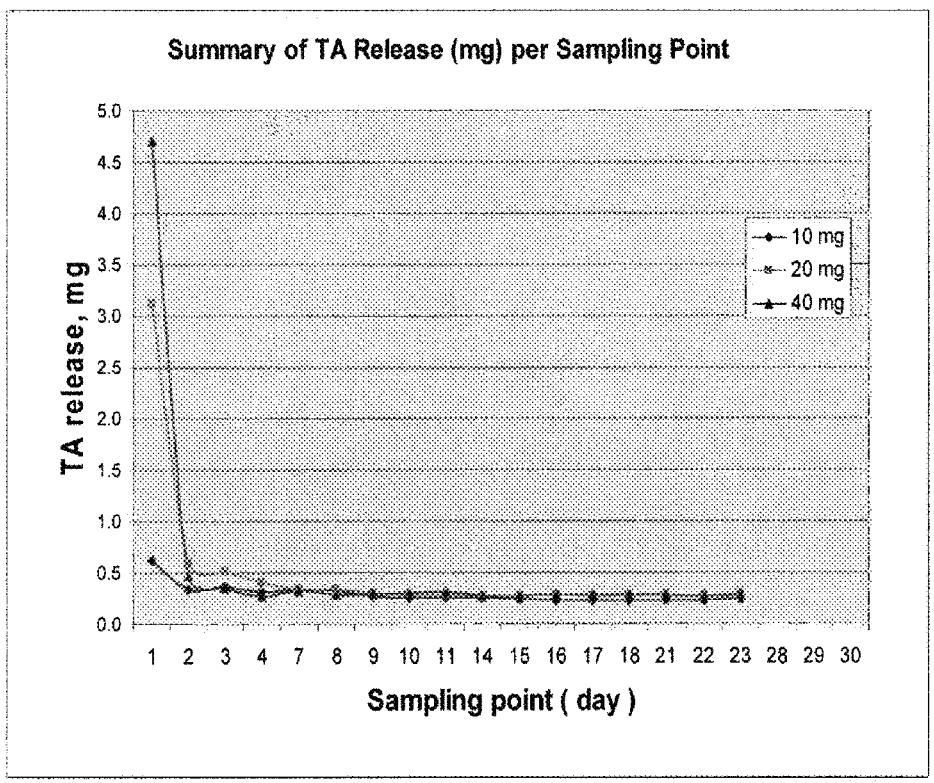
FIG. 1 is a plot of the amount of triamcinolone acetonide released per sampling time point for samples loaded with 10 mg, 20 mg and 40 mg triamcinolone acetonide respectively.

The present application provides, in part, a composition comprising an in situ crosslinkable modified hyaluronic acid, wherein the modified hyaluronic acid is a flowable liquid with an initial viscosity of between 2 and 150,000 mPa·s, wherein the hyaluronic acid polymerizes in situ and forms a hydrogel with an elastic modulus of less than 0.1 GPa, or less than 0.05 GPa, when the composition comprising the modified hyaluronic acid and initiator is applied on a tissue of a mammal. In certain aspects, the viscosity is between 10 and 50,000 mPa·s, or between about 50 and 10,000 mPa·s. In another aspect, the elastic modulus is 0.001 to about 0.1 GPa, or about 0.01 to 0.05 GPa.

In one aspect, the composition further comprises a crosslinking agent selected from the group consisting of polyethylene glycol diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate and glycerol 1,3-diglycerolate diacrylate sorbitol acrylate, and derivatives thereof. In one aspect, the modified hyaluronic acid comprises a formula:

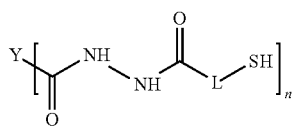

wherein: n≥2; Y comprises a residue of the hyaluronic acid; and L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group or a combination thereof. In another aspect, the composition further comprises a thiol comprising compound selected from the group consisting of N-acetyl cysteine, glutathione, 2,3-dimercapto-1-propanesulfonic acid and 2,3-dimercapto-1-propanesulfonic acid sodium salt monohydrate; or further comprises cysteine or a salt thereof. In another aspect, the composition further comprises a bioactive agent as solid particles. The bioactive agent may be a steroid. Also provided herein are kits comprising the compositions with an oxidant, and a buffer. Also provided herein is a method of treating a medical condition in a mammal in need thereof, the method comprising using the composition or kit as described herein, wherein the method comprises contacting the composition comprising the modified hyaluronic acid at a tissue site of the mammal. In certain aspect, the medical condition is osteoarthritis or is chronic sinusitis.

In another aspect, there is provided a composition comprising a thiol functionalized polysaccharide comprising a bioactive agent, wherein the polysaccharide is in a form of a bioresorbable polymer matrix and the bioactive agent is dispersed within the polymer matrix as a solid. In one variation, the solid is in the form of particles that are between 0.01 microns to 2,000 microns. In one variation, the thiol functionalized polysaccharide comprises a compound selected from the group consisting of:

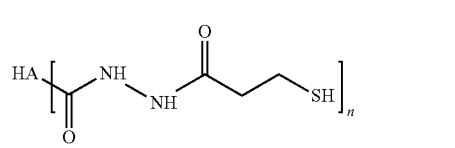  II

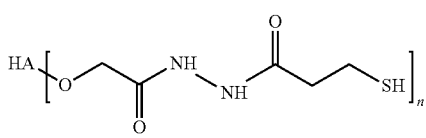  III

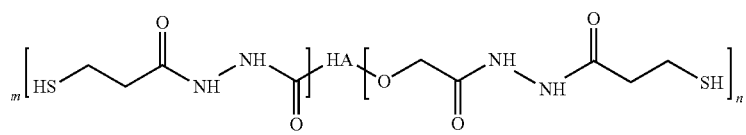  IV or mixtures thereof, wherein m≥2 and n≥2. In another variation, the thiol functionalized polysaccharide comprises a compound of the formulae:

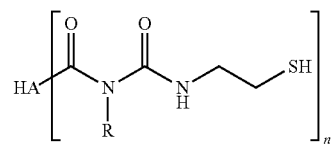  V

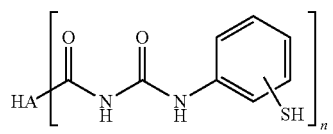  VI wherein HA is a residue of hyaluronic acid or a derivative thereof, R is $C_{1-5}$ alkyl and n≥2. In another variation, the thiol functionalized polysaccharide comprises a compound of the formulae:

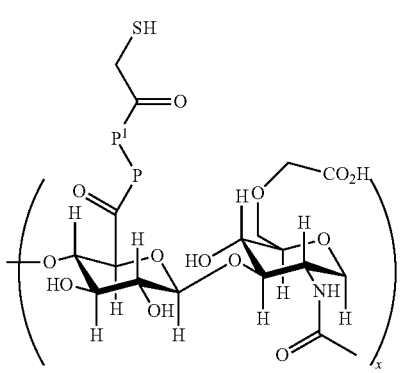  IIa

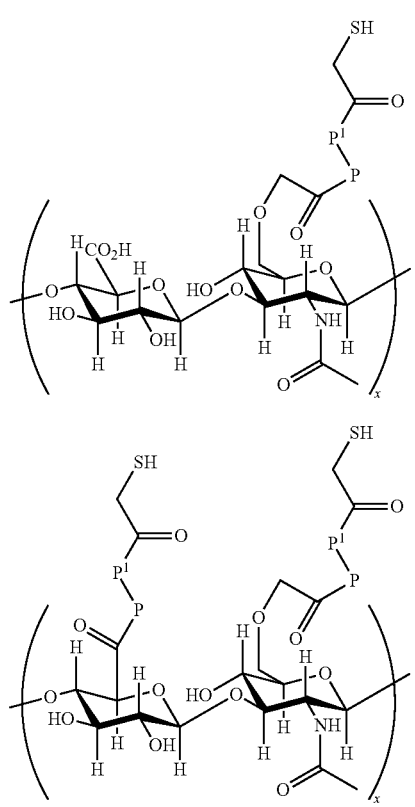

or mixtures of each of the above formulae.

In one embodiment, there is provided a kit comprising: a) a thiol functionalized polysaccharide; b) a biological active agent; and c) a buffer; wherein when the thiol functionalized polysaccharide, active agent and buffer are combined together, a crosslinked polysaccharide polymer matrix is obtained wherein the active agent is dispersed in the matrix as a solid. In certain variations, the kit comprises the compound and compositions as provided herein.

In another aspect, there is provided a composition comprising a bioresorbable polymer matrix and a bioactive agent prepared by polymerizing a suspension of a solid form of the bioactive agent suspended in the media containing precursors of polymerization. In a particular aspect, there is provided a composition comprising liquid precursor(s) of polymer matrix and a solid form of a bioactive agent wherein the precursor(s) are capable of forming an essentially non-flowing polymeric matrix. In another aspect, there is provided a composition comprising a polymeric matrix and a solid form of a bioactive agent, wherein up to half of the bioactive agent partitions into physiological fluid in 1 hour to 10,000 hours. In yet another aspect, there is provided a composition comprising a polymeric matrix and a solid form of a bioactive agent, wherein more than half of the bioactive agent partitions into physiological fluid in 1 hour to 10,000 hours. In another aspect, there is provided a composition comprising a polymeric matrix and a solid form of a bioactive agent, wherein the bioactive agent partitions into physiological fluid with the partitioning rate approximating zero-order kinetics. In another aspect, there is provided a composition comprising a polymeric matrix and a solid form of a bioactive agent, wherein the bioactive agent partitions into physiological fluid predominantly as a result of said polymer matrix degradation.

In yet another aspect, there is provided a method of preparing a bioactive agent formulation, wherein the agent is present in a solid form and, wherein the agent is occluded into a polymeric matrix by polymerization of polymer matrix precursors or by self assembly of the polymer. In another aspect, there is provided a method of treating a medical condition by delivering a bioactive agent onto the tissue site in the form of a formulation comprising bioresorbable polymeric matrix and solid form of the bioactive agent. Also provided is a kit for clinical use comprising a container containing a solid form of bioactive agent and a container comprising a precursor of a bioresorbable polymer matrix, wherein the bioactive agent is contacted with and polymerized with the precursor yielding a bioresorbable therapeutic polymeric matrix. The precursor may comprise of a single composition, two or more compositions in different containers, or a mixture of compositions in different containers that may be combined in situ to polymerize and yield the polymeric matrix. In one particular aspect, there is provided a composition for each of the above aspects and variations, wherein the bioactive agent is a steroid. In one variation of the above, the steroid is beclomethasone, beclomethasone dipropionate, budesonide, dexamethasone, methyl prednisolone, triamcinolone acetonide, triamcinolone hexacetonide and prednisolone. In another variation, the steroid is beclomethasone dipropionate or prednisolone. In certain variations, the composition is prepared by polymerizing a suspension, colloidal solution, slurry of other form of solid bioactive agent and from a liquid composition containing soluble monomers, pre-polymers or polymers and where the polymerization yields a polymer matrix containing solid form of bioactive agent. The solid bioactive agents may be present in the matrix in an occluded solid form. In other variations, each of the polysaccharides is in dry form. In certain aspects of the compounds, compositions and kits described herein, the modified hyaluronic acid is a thiol functionalized hyaluronic acid. In some embodiments, the composition comprising the polysaccharide may further comprises the biodegradable or bioresorbable polymer and copolymer compositions as described herein, or their mixtures thereof.

In one embodiment, there is provided a method for coupling two or more thiolated compounds comprising: a) contacting a first thiolated compound comprising the formula I:

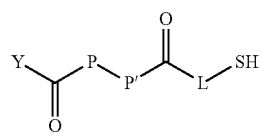

wherein: P and P' are each independently 0 or —NH—; Y comprises a residue of a macromolecule; and L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; b) with a second thiolated compound comprising a modified glycosaminoglycan comprising at least one SH group, and c) a third thiolated compound having a molecular weight of less than 300 Daltons and comprises at least one SH group, in the presence of an oxidant; wherein the first thiolated compound and second thiolated compound are the same or different compounds.

In one variation of the method, the macromolecule is selected from the group consisting of an oligonucleotide, a nucleic acid or a metabolically stabilized analogue thereof, a polypeptide, a lipid, a glycoprotein and a glycolipid, or a pharmaceutically-acceptable compound. In another aspect, the macromolecule is selected from the group consisting of a polysaccharide, a protein and a synthetic polymer. In yet another aspect, the polysaccharide comprises a sulfated-glycosaminoglycan. In another aspect, the macromolecule is selected from the group consisting of chondroitin, chondroitin sulfate, dermatan, dermatan sulfate, heparin, heparan sulfate, alginic acid, pectin and carboxymethylcellulose. In another variation, the macromolecule is a modified glycosaminoglycan. In one variation, the glycosaminoglycan is hyaluronan. In a particular variation of the compound, P and P' in the first and second thiolated compounds are —NH—. In one variation, L comprises a polyalkylene group having the formula $(CH_2)_n$, wherein n is from 1 to 20, or a polyether group having the formula $(—OCH_2CH_2—)_n$, wherein n is from 1 to 20. In another variation, the first and second thiolated compounds are selected from the group consisting of compounds IIa, IIIa and IVa, or mixtures thereof:

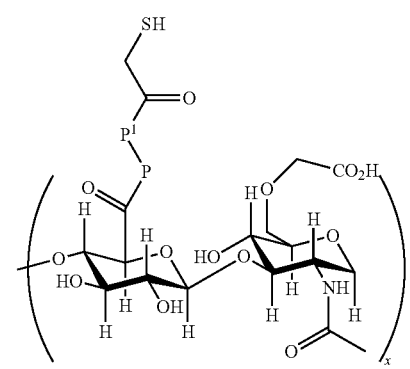

IIa

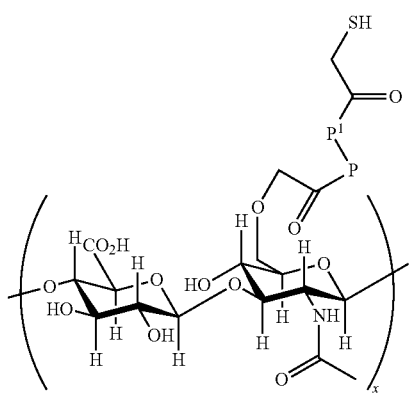

IIIa

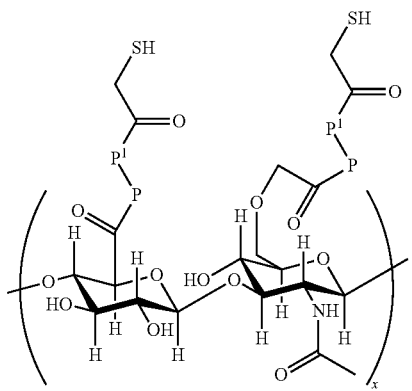

IVa wherein P and P' are each independently a bond, O or —NH—. In a particular variation of the method, P and P' are —NH—. In another variation, the oxidant is selected from the group consisting of molecular iodine, hydrogen peroxide, an alkyl hydroperoxide, a peroxy acid, a dialkyl sulfoxide, a high valent metal, a metal oxide and a halogen transfer agent. In another variation, the oxidant comprises a gas comprising oxygen, or wherein the oxidant further comprises hydrogen peroxide. In another aspect of the method, the third thiolated compound has a molecular weight of less than 200 Daltons. In another aspect, the third thiolated compound is selected from the group consisting of cysteine and glutathione or a mixture thereof. In another variation, the third thiolated compound comprises about 0.1 to about 1.0 mole or more equivalents of the first and second thiolated compound.

In another embodiment, there is provided a crosslinked macromolecular compound or composition comprising: a) a first thiolated compound comprising the formula I:

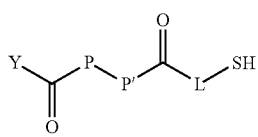

I wherein: P and P' are each independently O or —NH—; Y comprises a residue of a macromolecule; and L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; b) a second thiolated compound comprising a modified glycosaminoglycan comprising at least one SH group, and c) a third thiolated compound having a molecular weight of less than 300 Daltons and comprising at least one SH group; wherein the first thiolated compound and second thiolated compound are the same or different compounds. In another embodiment, there is provided a crosslinked macromolecular compound prepared from a method of coupling two or more thiolated compounds, the method comprising: a) contacting a first thiolated compound comprising the formula I:

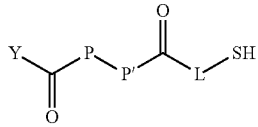

I wherein: P and P' are each independently O or —NH—; Y comprises a residue of a macromolecule; and L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; b) with a second thiolated compound comprising a modified glycosaminoglycan comprising at least one SH group, and c) a third thiolated compound having a molecular weight of less than 300 Daltons and comprising at least one SH group, in the presence of an oxidant; wherein the first thiolated compound and second thiolated compound are the same or different compounds. In one variation of the above, the macromolecule is selected from the group consisting of an oligonucleotide, a nucleic acid or a metabolically stabilized analogue thereof, a polypeptide, a lipid, a glycoprotein and a glycolipid, or a pharmaceutically-acceptable compound. In another variation, the macromolecule is selected from the group consisting of a polysaccharide, a protein and a synthetic polymer. In another variation, the polysaccharide comprises a sulfated-glycosaminoglycan. In another variation, the macromolecule is selected from the group consisting of chondroitin, chondroitin sulfate, dermatan, dermatan sulfate, heparin, heparan sulfate, alginic acid, pectin and carboxymethylcellulose. In a particular variation, the macromolecule is a modified glycosaminoglycan. In yet another aspect, the glycosaminoglycan is hyaluronan. In another variation, the compound forms a gel having a persistence to substantially maintain the shape and property of the gel in a neutral, aqueous solution at about 25° C. at pH 7 without degradation or dissolution in the aqueous solution for at least 48 hours. In a particular variation, the compound forms a gel having a persistence to maintain at least 75% of the shape and property of the gel without degradation or dissolution for at least 3 days, 5 days, 7 days, 14 days or 28 days. In another aspect, the compound forms a gel having a persistence to maintain at least 95% of the shape and property of the gel without degradation or dissolution for at least 3 days, 5 days, 7 days, 14 days or 28 days. In another embodiment, there is provided a pharmaceutical composition comprising a bioactive agent and the above crosslinked macromolecular compound or composition. In another embodiment, there is provided a composite comprising (1) a first macromolecular compound comprising a first anti-adhesion compound covalently bonded to a first anti-adhesion support, wherein the first-anti adhesion support comprises any of the above macromolecular compound or composition and (2) a first prohealing compound. In another embodiment, there is provided a terminally sterilized crosslinked macromolecular compound prepared from a method of coupling two or more thiolated compounds, the method comprising: a) contacting a first thiolated compound comprising the formula I:

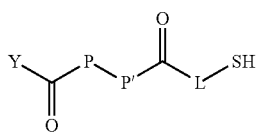

wherein: P and P' are each independently a bond, O or —NH—; Y comprises a residue of a macromolecule; and L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; b) with a second thiolated compound comprising a modified glycosaminoglycan comprising at least one SH group, and c) a third thiolated compound having a molecular weight of less than 300 Daltons and comprising at least one SH group, in the presence of an oxidant; wherein the first thiolated compound and second thiolated compound are the same or different compounds. In one variation the macromolecule is sterilized in the presence of one or more of ascorbic acid, ascorbate salt, DTT, EDTA, Trolox and sucrose. In another variation, the macromolecular compound is stable for at least two weeks. In another variation, the terminally sterilized crosslinked macromolecular compound is in dry form that is soluble in solution, wherein the macromoleculecular compound is partially crosslinked or is crosslinked. In another variation, the above terminally sterilized macromolecular compound further comprises a pharmaceutically active agent. In another variation, the active agent is a steroid. In one variation, the sterilized compound has a sterilization assurance level of $10^{-6}$. In another embodiment, there is provided a method for preparing a terminally sterilized macromolecular compound of as described above comprising: a) sealing an unsterilized macromolecular compound of the above in a container; and b) subjecting the macromolecular compound to electron beam irradiation or gamma irradiation at a dose sufficient to sterilize the composition; wherein the terminally sterilized macromolecular compound is in dry form and is soluble in solution. In another embodiment, there is provided a method for improving wound healing in a subject in need of such improvement, comprising contacting the wound of the subject with any of the above compound or composition. In yet another embodiment, there is provided a method for delivering at least one bioactive agent to a patient in need of such delivery, comprising contacting at least one tissue capable of receiving the bioactive compound with the above compound or composition. Further provided is the use of the above compound or composition as a growth factor, an anti-inflammatory agent, an anti-cancer agent, an analgesic, an anti-infection agent, or an anti-cell attachment agent. Further provided is the use of the above compound or composition to repair a tympanic membrane perforation. Further provided is the use of the above compound or composition to prevent sinus osteum closure during or after FESS, to promote healing after FESS, to reduce scarring after FESS, to prevent adhesion after a surgical procedure. In one variation of the above, the surgical procedure is selected from the group consisting of cardiosurgery and articular surgery, abdominal surgery, a surgical procedure performed in the urogenital region, a surgical procedure involving a tendon, laparascopic surgery, pelvic surgery, oncological surgery, sinus and craniofacial surgery, ENT surgery and a procedure involving spinal dura repair. In another aspect, there is provided the use of the above compound or composition to prevent airway stenosis and for vocal fold repair. In another aspect, the above compound and composition may be used to support the growth of primary cells or immortalized cells, to support the growth of tumor cells, fibroblasts, chondrocytes, stem cells, epithelial cells, neural cells, cells derived from the liver, endothelial cells, cardiac cells, muscle cells, or osteoblasts. In another aspect, there is the use of the above compound or composition for bone or cartilage repair, to extend the viability of skin, to promote scar-free wound healing after a surgical procedure. Also provided herein is an article coated with any of the above compound or composition. The article may be selected from the group consisting of a suture, a clap, a stent, a prosthesis, a catheter, a metal screw, a bone plate, a pin and a bandage. Also provided is a kit for a sterilized crosslinked macromolecular compound or composition comprising: a) the above macromolecular compound or composition in dry form that is soluble in solution; and b) one or more of a radiation stabilizer, an excipient, buffer or preservative. In one variation, the kit further comprises a crosslinking accelerant, or wherein the composition further comprises a pharmaceutically active agent. In one variation, the pharmaceutically active agent is a steroid. In another variation, the steroid is selected from the group comprising triamcinolone, triamcinolone diacetate, triamcinolone acetonide and triamcinolone hexacetonide.

Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as lyophilized powders for parenteral administration. Optionally, excipients, such as polyvinylpyrrolidinone, gelatin, hydroxycellulose, acacia, polyethylene glycol, mannitol, sodium chloride, or sodium citrate, may also be added. Pharmaceutically acceptable carriers may be added to enhance or stabilize the composition, or to facilitate preparation of the composition. Solid carriers include starch, lactose, calcium sulfate, dihydrate, terra alba, magnesium stearate or stearic acid, talc, pectin, acacia, agar, or gelatin. The pharmaceutical preparations are made following the conventional techniques of pharmacy. Suitable formulations for each of these methods of administration may be found in, for example, *Remington: The Science and Practice of Pharmacy*, A. Gennaro, ed., 21st edition, Lippincott, Williams & Wilkins, Philadelphia, Pa., 2006.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting. Before the present compounds, composites, compositions, and/or methods are disclosed and described, it is to be understood that the aspects described below are not limited to specific compounds, synthetic methods, or uses as such may vary. It is also to be understood that the terminology used herein is for the purpose of describing particular aspects only and is not intended to be limiting.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "hydrazide compound" as used herein is any compound having at least one hydrazide group having the formula $NH_2NRC(O)$—, wherein R can be hydrogen, a lower alkyl group, an amide group, a carbamate group, a hydroxyl group, or a halogen group.

The term "hydrazide-reactive group" as used herein is any group that can react with the primary or secondary amino group of the hydrazide group to form a new covalent bond. Examples of hydrazide-reactive groups include, but are not limited to, a ketone, an aldehyde, or an activated carboxylate group.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "bioactive polymer" means the polymer composition comprising the polymer, or the degradation products of the polymer that has an effect on living tissue, or that may have useful biological properties. The bioactive polymer may be bioactive in itself, and may be synergistically bioactive when employed in conjunction with the biologically active agent.

The term "bioresorbable polymer" means a polymer that is capable of being metabolized, degraded or broken down and resorbed and/or eliminated through normal biological actions or processes and excretory processes by the body. Such metabolized or break down products are preferably substantially non-toxic to the body, and such products may themselves be bioactive. As used herein, the bioresorbable polymers of the present application may also be bioactive polymers. See D. D. Allison and K. J. Grande-Allen, *Tissue Engineering*, Vol. 12, Number 8, 2131-2140 (2006).

The terms "bioabsorbable" or "biodegradable" as used herein interchangeably, refers to the ability of a tissue-compatible material to degrade in the body after implantation into nontoxic products that are eliminated from the body or metabolized. See, for example, Barrows, "*Synthetic Bioabsorbable Polymers,*" p. 243, In: High Performance Biomaterials—A comprehensive Guide to Medical and Pharmaceutical Applications, Michael Szycher, ed., Technomic Publishing, Lancaster, Pa., 1991. The term "crosslinking" refers to the compositions as described herein that form polymers or polymer compositions through reaction processes or polymerization processes, including physical crosslinking, chemical crosslinking or combination of both processes. As is known in the art, physical crosslinks may result from complexation, hydrogen bonding, desolvation, Van der Waals interactions, ionic bonding, etc. Chemical crosslinking may be mediated by a single or multiple precursor components that form a covalently crosslinked network, thereby providing physical integrity to the polymer matrix. The chemical crosslinking may be accomplished by any of a number of mechanisms, including free radical polymerization, condensation polymerization, anionic or cationic polymerization, step growth polymerization, etc. . . . . . A "crosslinkable" compound is a compound that is capable of undergoing crosslinking.

The term "hyaluronic acid" refers to hyaluronic acid or derivatives thereof.

The term "hydrophobic" refers to compounds or compositions which lack an affinity for water.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

"Persistence" character of a gel means the ability of the gel to substantially maintain the shape and property of the gel in a neutral, aqueous solution at about 25° C. at pH 7 without degradation or dissolution in the aqueous solution for an extended period of time. In certain aspects, depending on the nature and composition of the macromolecule, the gel maintains a persistence wherein at least 75%, 80%, 85%, 90%, 95%, 97%, 98% or 99% of the shape and property without degradation or dissolution for an extended period of time. In certain aspects, depending on the nature and composition of the macromolecule, the gel provides a composition that maintains persistence for an extended period of time, such as a period of at least about 24 hours, 36 hours, 48 hours or more. In certain aspects, the composition maintains persistence for a period of at least 3 days, 5 days, 10 days, 15 days 20 days, 25 day, 30 days and 2 months, 3 months, 4 months, 5 months and 6 months or more.

The term "polyethylene glycol" or "PEG" is sometimes also referred to as poly(ethylene oxide) (PEO) or poly(oxyethylene). These terms may be used interchangeably in the present application.

The term "polyanionic polysaccharide" (PAS) means a polysaccharide, including non-modified as well as chemical derivatives thereof, that contains more than one negatively charged group (e.g., carboxyl groups at pH values above about 4.0) and includes salts thereof, such as sodium or potassium salts, and alkaline earth metal salts such a calcium or magnesium salts.

"Therapeutically effective amount" means a drug amount that elicits any of the biological effects listed in the specification.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species.

The term "drug," or "pharmaceutically active agent" or "bioactive agents," as used interchangeably, means any organic or inorganic compound or substance having bioactivity and adapted or used for therapeutic purposes. Proteins, hormones, anti-cancer agents, oligonucleotides, DNA, RNA and gene therapies are included under the broader definition of "drug".

The term "solid" as used herein, means a non-fluid substance, including crystalline forms, their polymorphs, non-crystalline, amorphous substances, precipitates, and particles of the drug or bioactive agent. Each of these solid forms may vary in size, from about 0.01 microns to 2,000 microns, as disclosed herein.

"Peptide," "polypeptide," "oligopeptide" and "protein" are used interchangeably when referring to peptide or protein drugs (or as bioactive agents), and shall not be limited as to any particular molecular weight, peptide sequence or length, field of bioactivity or therapeutic use, unless specifically stated otherwise.

The term "poly(lactide-co-glycolide)" or "PLG" means a copolymer derived from the condensation copolymerization of lactic acid and glycolic acid, or, by the ring opening polymerization of -hydroxy acid precursors, such as lactide or glycolide. The terms "lactide," "lactate," "glycolide" and "glycolate" are used interchangeably as noted herein.

The term "pharmaceutically acceptable salts" refer to salts or complexes that retain the desired biological activity of the compounds (or drugs or biologically active agents) of the present invention and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art.

The term "polylactide" or "PLA" means a polymer derived from the condensation of lactic acid or by the ring opening polymerization of lactide. The terms "lactide" and "lactate" are used interchangeably.

The term "biodegradable polyesters" means any biodegradable polyesters, which are preferably made from monomers selected from the group consisting of D,L-lactide, D-lactide, L-lactide, D,L-lactic acid, D-lactic acid, L-lactic acid, glycolide, glycolic acid, caprolactone, hydroxy hexanoic acid, butyrolactone, hydroxybutyric acid, valerolactone, hydroxy valeric acid, hydroxybutyric acids, malic acid and copolymers thereof.

The term "thrombin" as used herein, includes natural thrombin molecules derived from animal or human plasma, and synthetic forms such as those produced by recombinant DNA technology including functionally active analogs that effectively maintain clotting activity in an animal or human.

Bioresorbable Polymers:

The patents below disclose various bioresorbable polymer compositions that may be employed in the present application.

The biodegradable polymer chains useful in the invention preferably have molecular weights in the range 500 to 5,000,000. The biodegradable polymers can be homopolymers, random or block copolymers. The copolymer can be a random copolymer containing a random number of subunits of a first copolymer interspersed by a random number of subunits of a second copolymer. The copolymer can also be block copolymer containing one or more blocks of a first copolymer interspersed by blocks of a second copolymer. The block copolymer can also include a block of a first copolymer connected to a block of a second copolymer, without significant interdispersion of the first and second copolymers. Such polymers are known in the art, and described, for example, in U.S. Pat. No. 6,793,938.

Biodegradable homopolymers that may be useful in the present application may comprise of monomer units selected from the following groups: hydroxy carboxylic acids such as α-hydroxy carboxylic acids including lactic acid, glycolic acid, lactide (intermolecularly esterified dilactic acid), and glycolide (intermolecularly esterified diglycolic acid); β-hydroxy carboxylic acids including β-methyl-β-propiolactone; γ-hydroxy carboxylic acids δ-hydroxy carboxylic acids; and ε-hydroxy carboxylic acids including ε-hydroxy caproic acid; lactones such as: β-lactones; γ-lactones; δ-lactones including valerolactone; and ε-lactones such as ε-caprolactone; benzyl ester-protected lactones such as benzyl malolactone; lactams such as: β-lactams; γ-lactams; δ-lactams; and ε-lactams; thiolactones such as 1,4-dithiane-2,5-dione; dioxanones; unfunctionalized cyclic carbonates such as: trimethylene carbonate, alkyl substituted trimethylene carbonates and spiro-bis-dimethylene carbonate (2,4,7,9-tetraoxaspiro [5.5]undecan-3,8-dione); anhydrides; substituted N-carboxy anhydrides; propylene fumarates; orthoesters; phosphate esters; phosphazenes; alkylcyanoacrylates; aminoacids; polyhydroxybutyrates; and substituted variations of the above monomers.

The use of such monomers results in homopolymers such as polylactide, polyglycolide, poly(p-dioxanone), polycaprolactone, polyhydroxyalkanoate, polypropylenefumarate, polyorthoesters, polyphosphate esters, polyanhydrides, polyphosphazenes, polyalkylcyanoacrylates, polypeptides, or genetically engineered polymers, and other homopolymers which can be formed from the above mentioned examples of monomers. Combinations of these homopolymers can also be used to prepare the pharmaceutical compositions of the present application.

The biodegradable copolymers can be selected from poly (lactide-glycolide), poly(p-dioxanone-lactide), poly(p-dioxanone-glycolide), poly(p-dioxanone-lactide-glycolide), poly (p-dioxanone-caprolactone), poly(p-dioxanone-alkylene carbonate), poly(p-dioxanone-alkylene oxide), poly(p-dioxanone-carbonate-glycolide), poly(p-dioxanone-carbonate), poly(caprolactone-lactide), poly(caprolactone-glycolide), poly(hydroxyalkanoate), poly(propylenefumarate), poly (ortho esters), poly(ether-ester), poly(ester-amide), poly(ester-urethane), polyphosphate esters, polyanhydrides, poly (ester-anhydride), polyphospazenes, polypeptides or genetically engineered polymers. Combinations of these copolymers can also be used to prepare the polymers of the pharmaceutical compositions of the invention.

In certain aspects of the present application, the biodegradable polymers are polylactide and poly(lactide-glycolide). In some lactide-containing embodiments, the polymer may be prepared by polymerization of a composition including lactide that are optically active and/or optically inactive (i.e., racemic [D,L]-lactide and meso [D,L]-lactide). For example, the composition may contain, for example, 50% racemic and 50% optically active lactide.

Many nontoxic bioabsorbable homopolymers, copolymers and terpolymers, that are fluids at body temperature, may be used as a sustained or extended release carrier for intramuscular or subcutaneous injectables. In particular, there are a number of subclasses of the above polymers that are lactone polymers (including polymers which contain two or more monomers) composed of one or more lactone monomers selected from the group consisting of glycolide, L-lactide, D,L-lactide, 1,4-dioxanone, ε-caprolactone, 1,5-dioxepan-2-one and trimethylene carbonate and other commonly used lactone monomers that are fluids at body temperature. These polymers may be linear, branched, or star branched; statistically random copolymers or terpolymers; segmented block copolymers or terpolymers. Examples of suitable terpolymers are terpolymers containing co-monomer combinations selected from the group consisting of glycolide, L-lactide, and p-dioxanone; glycolide, ε-caprolactone and p-dioxanone; and L-lactide, ε-caprolactone and p-dioxanone. These polymers should be purified to remove unreacted monomer which may cause an inflammatory reaction in tissue. Such polymers are known in the art, and described, for example, in U.S. Pat. No. 5,653,992.

Preferred polymers for use as sustained or extended release carriers are lactone polymers selected from the group consisting of poly(lactide-co-ε-caprolactone), poly(lactide-co-p-dioxanone), poly(lactide-co-1,5-dioxepan-2-one), poly(ε-caprolactone-co-p-dioxanone) and poly(1,5-dioxepan-2-one-co-p-dioxanone). The co-monomer ratios of these copolymers may be in the range of from about 70:30 mole percent to about 30:70 mole percent and preferably in the range of from 40:60 mole percent to 60:40 mole percent of the first monomer to second monomer. In certain embodiments, these polymers may be random copolymers.

In one embodiment, the copolymer carriers of this invention are characterized by being liquids at about 37° C. (body temperature) and may also be liquids at about 25° C. in the absence of solvents or other liquids or solutions. In particular aspects of the present application, the copolymers of the present invention may have an inherent viscosity (as determined in a 0.1 g/dL solution of hexafluoroisopropanol (HFIP) at 25° C.) ranging from about 0.05 to about 0.8 dL/g, or from about 0.05 to about 0.3 dL/g. A copolymer with an inherent viscosity below 0.05 dL/g may fail to significantly impart a controlled release profile to a pharmaceutical, and a carrier copolymer with an inherent viscosity above 0.8 dL/g may be too viscous to be easily administered. In another particular embodiment of the present application, the biodegradable material is a lactide/glycolide copolymer, and the material may be in a range of 60% 70% lactide. Examples of other suitable materials include poly(dl-lactide), poly(1-lactide), polyglycolide, poly(dioxanone), poly(glycolide-co-trimethylene carbonate), poly(1-lactide-co-glycolide), poly(dl-lactide-co-glycolide), poly(1-lactide-co-dl-lactide) and poly (glycolide-co-trimethylene carbonate-co-dioxanone). Such polymers are known in the art, and described, for example, in U.S. Pat. No. 7,112,214.

In another particular embodiment, the biocompatible and bioabsorbable polymer may be at least one polymer selected from the group consisting of polyglycolic acid, polyglycolic acid/poly-L-lactic acid copolymers, polycaprolactive, polyhydroxybutyrate/hydroxyvalerate copolymers, poly-L-lactide, polydioxanone, polycarbonates and polyanhydrides. Such polymers are known in the art, and described, for example, in U.S. Pat. No. 7,070,607.

In certain embodiments of the present application, the bioabsorbable polymers are liquid polymers. The synthetic, bioabsorbable, biocompatible polymers utilized in the present application are the reaction product of a polybasic acid or derivative thereof, a fatty acid, and a polyol, and may be classified as alkyd polyester liquids. In certain embodiments, the polymers of the present application are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible. In certain embodiments, the polymers utilized in the present application may have a weight average molecular weight of about 1,000 daltons and about 100,000 daltons. In one particular aspect, the polymers comprise an aliphatic polyester backbone with pendant fatty acid ester groups having relatively low melting points, e.g. less than about 40° C., or less than about 25° C.

In certain embodiments, the fatty acids used to prepare polymers of the present application may be saturated or unsaturated, and the carbon chain of the acids may vary in length from $C_4$ to $C_{12}$ for saturated fatty acids, and $C_4$ to $C_{22}$ for unsaturated fatty acids. Non-exclusive examples of such fatty acids include stearic acid, palmitic acid, myrisitic acid, caproic acid, decanoic acid, lauric acid, linoleic acid and oleic acid. Non-exclusive examples of polyols that may be used to prepare the polymers include glycols, polyglycerols, polyglycerol esters, glycerol, sugars and sugar alcohols. In one aspect, glycerol is a preferred polyhydric alcohol. Monoglycerides which may be used to prepare liquid polymers utilized in the present invention include, without limitation, monostearoyl glycerol, monopahnitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monocaproyl glycerol, monodecanoyl glycerol, monolauroyl glycerol, monolinoleoyl glycerol and monooleoyl glycerol.

Polybasic acids that may be used include natural multifunctional carboxylic acids, such as succinic, glutaric, adipic, pimelic, suberic and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. In certain embodiments of the present application, the polymer may be prepared from the polybasic acid or derivative thereof, the monoglyceride and, additionally or optionally, at least on additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

Copolymers containing other linkages, in addition to an ester linkage also may be prepared. Non-exclusive examples include ester-amides, ester-carbonates, ester-anhydrides and ester urethanes.

Functionalized polymers may be prepared by appropriate choice of monomers. In another aspect, polymers having pendant hydroxyls can be prepared using a hydroxy acid such as malic or tartaric acid in the synthesis. Similarly, polymers with pendant amines, carboxyls or other functional groups also may be prepared.

In another embodiment, the polymers of the present invention may be endcapped in a variety of ways to obtain the desired properties. Endcapping reactions convert the terminal and pendant functional groups, such as hydroxyl groups and terminal carboxyl groups, into other types of chemical moieties. Typical endcapping reactions include but are not limited to alkylation and acylation reactions using common reagents such as alkyl, alkenyl, or alkynyl halides and sulfonates, acid chlorides, anhydrides, mixed anhydrides, alkyl and aryl isocyanantes and alkyl and aryl isothiocyantes. Endcapping reactions can impart new functionality to the polymers of the present application. For example, when acryloyl or methacryloyl chloride is used to endcap the polymers of the present application, the corresponding acrylate or methacrylate ester groups, respectively, are generated that may be subsequently polymerized to form a crosslinked network.

The polymerization of the alkyd polyester polymers may be performed under melt polycondensation conditions in the presence of a catalyst at room temperature or above room temperature. The catalyst may be a metal or an organometallic catalyst. The catalyst may be used in the mixture at a molar ratio of polyol and polycarboxylic acid to catalyst in the range of from about 10,000/1 to 100,000/1. The reaction may be performed at above room temperature, preferably at about 35° C. or about 50° C., or above 100° C. and less than about 150° C. The exact reaction conditions, including the catalyst, the mole ratio and the reaction temperature chosen will depend on numerous factors, including the properties of the polymer desired, the viscosity of the reaction mixture, and melting temperature of the polymer. The preferred reaction conditions of temperature, time and pressure can be readily determined by assessing these and other factors.

In another embodiment of the present application, the bioabsorbable polymer is a polyanionic polysaccharide. Non-exclusive examples of polyanionic polysaccharides or glycosaminoglycans that may be employed in the composition of the present application include, hyaluronic acid (HA), carboxymethylcellulose (CMC) carboxymethylamylose (CMA), chondroitin-4-sulfate, chondroitin-6-sulfate, dermatin sulfate, dermatin-6-sulfate, heparin sulfate, heparin, keratin sulfate and their derivatives, and combinations thereof. Such polymers are known in the art, and described, for example, in U.S. Pat. No. 6,056,970.

In a particular embodiment, the polyanionic polysaccharide is HA, CMC or CMA which is in the form of a water-insoluble derivative. A "polyanionic polysaccharide derivative," as the term is used herein, means one or more polyanionic polysaccharides (PAS) that are chemically modified from the native form. Such chemical modifications may include the addition of functional groups (e.g., substituted amide groups, ester and amine groups); reactions that increase the water insolubility of the PAS by covalently cross-linking the PAS molecules; and reactions that increase the water-insolubility of the PAS by noncovalent interactions. Additionally, the hemostatic composition can include two or more polyanionic polysaccharides or their water-insoluble derivatives, e.g. HA and CMC or HA and CMA.

In another particular embodiment, the polyanionic polysaccharide may be combined with one or more hydrophobic bioabsorbable polymers or copolymers. Preferably, the hydrophobic bioabsorbable polymer is chosen from the group consisting of polyglycolide, polylactide (D, L or DL), polydioxanones, polyestercarbonates, polyhydroxyalkonates, polycaprolactone (polylactones), and copolymers thereof. More preferably, the polymer is selected from the group consisting of polyglycolide, polylactide and copolymers of polyglycolide-caprolactone, polyglycolide-polylactide, or polylactide-polycaprolactone. The concentration of hydrophobic bioabsorbable polymer used in combination with the polyanionic polysaccharide is preferably in the range of 0.1 to 50 mg/cm$^2$.

In another embodiment, the polymers are injectable, bioabsorbable polymers. The polymer are selected from the group consisting of liquid polymers of at least two first repeating units and liquid polymers of a plurality of first lactone and second lactone repeating units; wherein the first lactone repeating units are selected from the group consisting of ε-caprolactone repeating units, trimethylene carbonate repeating units, ether lactone repeating units (that is, 1,4-dioxepan-2-one and 1,5-dioxepan-2-one) and combinations thereof and the second lactone repeating units are selected from the group consisting of glycolide repeating units, lactide repeating units (that is, defined as L-lactide, D-lactide or D,L-lactide repeating units), p-dioxanone repeating units and combinations thereof. Such polymers are known in the art, and described, for example, in U.S. Pat. No. 5,824,333.

In another embodiment, there is provided a biodegradable copolymer composition having reverse thermal gelation properties, wherein the composition comprises a mixture or blend of at least two types of biodegradable polyester (A-block)/polyethylene glycol (B-block) ABA or BAB triblock copolymer components in a proper ratio so that the mixture has the desired reverse thermal gelation properties. The first component of the triblock copolymer mixture may have an average molecular weight of between about 2500 and about 8000, preferably 3000 to 6500, and consists of a biodegradable polyester A-polymer block and a polyethylene glycol (PEG) B-polymer block in a ratio by weight of 1.3 to 3.0, or about 1.8 to 2.6. The second component of the triblock copolymer has an average molecular weight of between about 800 and about 7200, preferably 1500 to 6000, and consists of a biodegradable polyester A-polymer block and a polyethylene glycol (PEG) B-polymer block in a ratio by weight of 0.35 to 2.6, or about 0.55 to 2.5. Such polymers are known in the art, and described, for example, in U.S. Pat. No. 7,135,190. Preferably, the biodegradable polyester may be prepared from monomers selected from the group consisting of D,L-lactide, D-lactide, L-lactide, D,L-lactic acid, D-lactic acid, L-lactic acid, glycolide, glycolic acid, -caprolactone, -hydroxy hexanoic acid, -butyrolactone, -hydroxy butyric acid, -valerolactone, -hydroxy valeric acid, hydroxybutyric acids, malic acid, and copolymers thereof. In a particular aspect of the present application, the biodegradable polyester is synthesized from monomers selected from the group consisting of D,L-lactide, D-lactide, L-lactide, D,L-lactic acid, D-lactic acid, L-lactic acid, glycolide, glycolic acid, -caprolactone, -hydroxy hexanoic acid, and copolymers thereof. In another particular aspect, the biodegradable polyester may be prepared from monomers selected from the group consisting of D,L-lactide, D-lactide, L-lactide, D,L-lactic acid, D-lactic acid, L-lactic acid, glycolide, glycolic acid, and copolymers thereof. In certain aspect of the present application, the A-block copolymers are generally lactide or lactide-co-glycolide moieties. Unless specifically referred to otherwise, the terms "lactide", "lactate", or "L" as used herein shall include all lactic acid derivatives and "glycolide," "glycolate" or "G" shall include all glycolic acid derivatives.

In the hydrophobic polyester A-block of both the first and second components, the molar ratio of lactate content to glycolate content (L:G ratio) is between about 3:1 and about 1:0, preferably between about 1:1 and about 1:0.

The average molecular weight of PEG in the first component is in a range of 900 to 2000, preferably 1000 to 1450. The average molecular weight of PEG in the second component is in a range of 600 to 2000, preferably 900 to 1450. In certain aspects of the present application, the first component has a lower gelation temperature than the second component.

Mixing of two or more types of ABA or BAB triblock polyester polyethylene glycol copolymers may be performed by mixing two or more individually prepared tri-block copolymers, or by preparing two or more tri-block copolymers in one reaction container or vessel. The mixture of copolymers resulting from the above two processes may have the same or different gelation properties. In the latter method, both polymers have polyester A blocks with the same lactide/glycolide ratio, molecular weight and polydispersity.

Exemplary bioresorbable polymers as described herein include both non-crosslinked as well as crosslinked polymers.

Non-exclusive examples of non-crosslinked polymers, for example, may include synthetically produced resorbable block copolymers of poly($\alpha$-hydroxy-carboxylic acid)/poly(oxyalkylene). See U.S. Pat. No. 4,826,945. These copolymers are not crosslinked and are water-soluble so that the body can excrete the degraded block copolymer compositions. See for example, Younes et al., J. Biomed. Mater. Res. 21: 1301 1316 (1987); and Cohn et al., J. Biomed. Mater. Res. 22: 993 1009 (1988). Presently preferred bioresorbable polymers include one or more components selected from poly (esters), poly(hydroxy acids), poly(lactones), poly(amides), poly(ester-amides), poly(amino acids), poly(anhydrides), poly(orthoesters), poly(carbonates), poly(phosphazines), poly(phosphoesters), poly(thioesters), polysaccharides and mixtures thereof. With respect to the poly(hydroxy) acids, polylactic acid, polyglycolic acid, polycaproic acid, polybutyric acid, polyvaleric acid and copolymers and mixtures thereof are preferred.

Macromolecules

A macromolecule as disclosed herein is any compound having at least one hydrazide-reactive group and/or aminooxy-reactive group. Examples of hydrazide-reactive groups and aminooxy-reactive groups include, but are not limited to, a carboxyl group including the salt or ester thereof or an amide group. The hydrazide-reactive group or the aminooxy-reactive group can be naturally present on the macromolecule, or the macromolecule can be chemically modified to incorporate the hydrazide-reactive group or the aminoalkoxy-reactive group on the macromolecule. In one aspect, the macromolecule is an oligonucleotide, a nucleic acid or a metabolically stabilized analogue thereof, a polypeptide, a lipid, a glycoprotein, or a glycolipid. In another aspect, the macromolecule is a polysaccharide, a protein, or a synthetic polymer. Present preferred bioresorbable polymers also include the modified macromolecules comprising hydrazide-reactive group and/or aminooxy-reactive groups as disclosed in PCT/US/2004/040726 (WO 2005/056608) and U.S. Publication 2008/0025950. In particular, the macromolecules may comprise oligonucleotide, nucleic acid, polypeptide, lipid, glycoprotein, glycolipid, polysaccharide, protein, synthetic polymers, and glycosaminoglycan. In particular, the glycosaminoglycan may be hyaluronan. In a particular polymer composition, the composition is CARBYLAN-S® as disclosed in the above cited PCT and U.S. applications, the subject matter disclosed in this publication is hereby incorporated by reference in its entirety.

Polysaccharides

Any polysaccharide known in the art can be used herein. Examples of polysaccharides include starch, cellulose, glycogen or carboxylated polysaccharides such as alginic acid, pectin, or carboxymethylcellulose. In one aspect, the polysaccharide is a glycosaminoglycan (GAG). A GAG is one molecule with many alternating subunits. For example, HA is (GlcNAc-GlcUA-)x. Other GAGs are sulfated at different sugars. Generically, GAGs are represented by the formula A-B-A-B-A-B, where A is a uronic acid and B is an aminosugar that is either O- or N-sulfated, where the A and B units can be heterogeneous with respect to epimeric content or sulfation.

There are many different types of GAGs, having commonly understood structures, which, for example, are within the disclosed compositions, such as chondroitin, chondroitin sulfate, dermatan, dermatan sulfate, heparin, or heparan sulfate. Any GAG known in the art can be used in any of the methods described herein. Glycosaminoglycans can be purchased from Sigma, and many other biochemical suppliers. Alginic acid, pectin, and carboxymethylcellulose are among other carboxylic acid containing polysaccharides useful in the methods described herein. In one aspect, the polysaccharide is hyaluronan (HA). HA is a non-sulfated GAG. Hyaluronan is a well known, naturally occurring, water soluble polysaccharide composed of two alternatively linked sugars, D-glucuronic acid and N-acetylglucosamine. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., and many other suppliers. For high molecular weight hyaluronan it is often in the range of 100 to 10,000 disaccharide units. In another aspect, the lower limit of the molecular weight of the hyaluronan is from about 1,000 Da, 2,000 Da, 3,000 Da, 4,000 Da, 5,000 Da, 6,000 Da, 7,000 Da, 8,000 Da, 9,000 Da, 10,000 Da, 20,000 Da, 30,000 Da, 40,000 Da, 50,000 Da, 60,000 Da, 70,000 Da, 80,000 Da, 90,000 Da, or 100,000 Da, and the upper limit is 200,000 Da, 300,000 Da, 400,000 Da, 500,000 Da, 600,000 Da, 700,000 Da, 800,000 Da, 900,000 Da, 1,000,000 Da, 2,000,000 Da, 4,000,000 Da, 6,000,000 Da, 8,000,000 Da or 10,000,000 Da where any of the lower limits can be combined with any of the upper limits.

Modified-Glycosaminoglycans

In one aspect, any glycosaminoglycan in the art can be chemically modified so that at least one of the hydroxyl groups present on the glycosaminoglycan is substituted with a hydrazide-reactive group to produce a modified-glycosaminoglycan. Glycosaminoglycans in general possess a plurality of hydroxyl groups. The phrase "at least one of the hydroxyl groups present on the glycosaminoglycan is chemically substituted with a hydrazide-reactive group or aminooxy-reactive group" as used herein refers to replacing or substituting hydrogen of the hydroxyl group with the hydrazide-reactive group or the aminooxy-reactive group via a chemical manipulation of the hydroxyl group present on the glycosaminoglycan.

In one embodiment, the polymer composition of the present application is a hydrogel formulation that may be used as a matrix composition. The matrix composition may be susceptible to certain enzymatic degradation processes, by hydrolytic degradation processes, or combinations thereof. In particular aspects, the polymer composition comprises hyaluronan (HA) that, when the polymer is degraded, the resulting composition is known to have inherent biological properties such as being an element in embryonic development, tissue organization, wound healing, angiogenesis and tumorigenesis. See D. D. Allison and K. J. Grande-Allen, *Tissue Engineering*, Vol. 12, Number 8, 2131-2140 (2006); G. D. Prestwich et al, *Tissue Engineering*, Vol. 12, Number 8, 2171-2180 (2006); G. D. Prestwich et al, *Tissue Engineering*, Vol. 12, Number 12, 3405-3416 (2006).

In one aspect, after the macromolecule has reacted with the aminooxy ether compound, the resultant modified macromolecule has at least one fragment having the formula

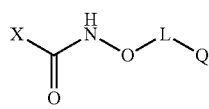

wherein X can be a residue of macromolecule; Q can be a bioactive agent, an aminooxy group, a SH group, or a thiol-reactive electrophilic functional group; and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group or a combination thereof.

In another aspect, the hydrazide-modified macromolecule comprises at least one unit comprising the formula

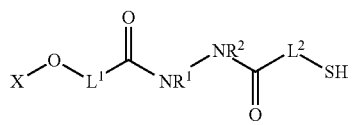

wherein X comprises a residue of a macromolecule; and $R^1$ and $R^2$ comprise, independently, hydrogen, a substituted or unsubstituted hydrocarbyl group, a substituted or unsubstituted heterohydrocarbyl group, or a polyether group; $L^1$ and $L^2$ comprise, independently, a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group, or a combination thereof. In one aspect of formula, $R^1$ and $R^2$ are hydrogen. In another aspect of the above formula, $L^1$ and $L^2$ are an alkylene group. Examples of alkylene groups can be denoted by the formula $-(CH_2)_n-$, where n is an integer from 1 to 20, 1 to 15, 1 to 10, 1 to 8, 1 to 6 or 1 to 4. In another aspect, $L^1$ is $CH_2$ and $L^2$ is $CH_2CH_2$. In one aspect, X in the above formula comprises chondroitin, chondroitin sulfate, dermatan, dermatan sulfate, heparin, heparan sulfate, alginic acid, pectin or hyaluronan. In another aspect of the above formula, X is hyaluronan, $R^1$ and $R^2$ are hydrogen, $L^1$ is $CH_2$, and $L^2$ is $CH_2CH_2$. This compound is referred to herein as Carbylan™-S.

In another aspect, a compound having at least one unit of the above formula can be produced by the process comprising (1) reacting a compound comprising the formula

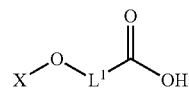

wherein X comprises a residue of a macromolecule; and $L^1$ comprises a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group, or a combination thereof, with a compound comprising the formula

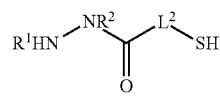

wherein $R^1$ and $R^2$ comprise, independently, hydrogen, a substituted or unsubstituted hydrocarbyl group, a substituted or unsubstituted heterohydrocarbyl group, or a polyether group, and $L^2$ comprises a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group or a combination thereof.

Crosslinked Macromolecules

Described below are methods and compositions for crosslinking any of the modified macromolecules described herein to produce a physiologically compatible macromolecular scaffold useful as a therapeutic aid. "Crosslinking" is defined herein as the ability of two or more macromolecules to produce a pore-containing matrix, where the macromolecules can be the same or different. One or more of macromolecules can be modified using any of the methods and compositions described herein. The use of additional compounds that will facilitate crosslinking are also included herein.

Oxidative Coupling

In general, oxidative coupling involves reacting two or more compounds that each have a SH group in the presence of an oxidant. It is also contemplated that the thiolated compound can couple with itself as well as the other thiolated compound. The reaction between the two SH groups produces a new disulfide bond (—S—S—). In one aspect, the oxidative coupling of a first thiolated compound Y—SH and a second thiolated compound G-SH produces a compound having the fragment

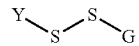

wherein Y can be a residue of any macromolecule described herein such as a modified-glycosaminoglycan and G is a residue of the thiolated compound. Depending upon the selection of the macromolecule, the macromolecule can be chemically modified so that the macromolecule has at least on SH group. For example, any naturally-occurring COOH groups or COOH groups added to the macromolecule can be converted to a thiol group using the techniques described herein including, but not limited to, the hydrazide and aminooxy methods described herein.

The second thiolated compound G-SH is any compound having at least one thiol group. The first and second thiolated compounds can be the same or different compounds. In one aspect, the second thiolated compound can be any macromolecule described above. In one aspect, the second thiolated compound is a polysaccharide having at least one SH group. Any of the polysaccharides described above can be used as the second thiolated compound. In another aspect, the second thiolated compound can be a sulfated-glycosaminoglycan. In a further aspect, the second thiolated compound includes chondroitin, chondroitin sulfate, dermatan, dermatan sulfate, heparin, heparan sulfate, alginic acid, pectin, carboxymethylcellulose or hyaluronan, wherein each of these compounds has at least one SH group.

The reaction between the first and second thiolated compounds is performed in the presence of an oxidant. In one aspect, the reaction between the first and second thiolated compounds can be conducted in the presence of any gas that contains oxygen. In one aspect, the oxidant is air. This aspect also contemplates the addition of a second oxidant to expedite the reaction. In another aspect, the reaction can be performed under an inert atmosphere (i.e., oxygen free), and an oxidant is added to the reaction. Examples of oxidants useful in this method include, but are not limited to, molecular iodine, hydrogen peroxide, alkyl hydroperoxides, peroxy acids, dialkyl sulfoxides, high valent metals such as $Co^{+3}$ and $Ce^{+4}$, metal oxides of manganese, lead, and chromium, and halogen transfer agents. The oxidants disclosed in Capozzi, G.; Modena, G. In *The Chemistry of the Thiol Group Part II*; Patai, S., Ed.; Wiley: New York, 1974; pp 785-839, which is incorporated by reference in its entirety, are useful in the methods described herein.

The reaction between the first and second thiolated compounds can be conducted in a buffer solution that is slightly basic. The amount of the first thiolated compound relative the amount of the second thiolated compound can vary. In one aspect, the volume ratio of the first thiolated compound to the second thiolated compound is from 99:1, 90:10, 80:20, 70:30, 60:40, 50:50, 40:60, 30:70, 20:80, 10:90 or 1:99. In one aspect, the first and second thiolated compounds react in air and are allowed to dry at room temperature. In this aspect, the dried material can be exposed to a second oxidant, such as hydrogen peroxide. The resultant compound can then be rinsed with water to remove any unreacted first and/or second thiolated compound and any unused oxidant. One advantage of preparing coupled compound via the oxidative coupling methodology described herein is that crosslinking can occur in an aqueous media under physiologically benign conditions without the necessity of additional crosslinking reagents.

In one aspect, described herein is a method for coupling two or more thiolated compounds by reacting a first thiolated compound having the formula

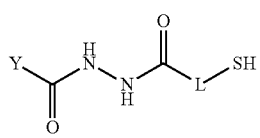

wherein Y can be a residue of any modified-glycosaminoglycan described herein, and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof, with a second thiolated compound having at least one SH group in the presence of an oxidant, wherein the first thiolated compound and second thiolated compound are the same or different compounds. In one aspect, the second thiolated compound has the above formula. In a further aspect, the first and second thiolated compounds are the same compound. The reaction between the thiolated compound having the above formula and the second thiolated compound produces a crosslinked compound having the fragment

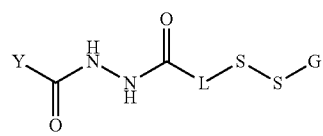

where Y and L are as defined above. In one aspect, L in the above formula can be $CH_2$, $CH_2CH_2$, or $CH_2CH_2CH_2$. In another aspect, G can be a polysaccharide residue such as, for example, a sulfated-glycosaminoglycan residue. In another aspect, G can be a residue of chondroitin, chondroitin sulfate, dermatan, dermatan sulfate, heparin, heparan sulfate, alginic acid, pectin, or carboxymethylcellulose or hyaluronan.

In another aspect, described herein is a method for coupling two or more thiolated compounds by reacting a first thiolated compound having the formula

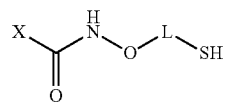

wherein X can be a residue of any macromolecule described herein and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof, with a second thiolated compound having at least one SH group in the presence of an oxidant, wherein the first thiolated compound and second thiolated compound are the same or different compounds.

In one aspect, X is a residue of any modified-glycosaminoglycan described herein. In another aspect, X can be a residue of hyaluronan. In one aspect, the second thiolated compound has the above formula. In a further aspect, the first and second thiolated compounds are the same compound. The reaction between the thiolated compound having the above formula and the second thiolated compound produces a crosslinked compound having the fragment

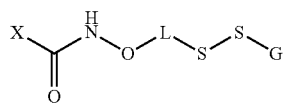

where X and L can be any macromolecule and linker, respectively, described herein. In one aspect, X is a modified-glycosaminoglycan described herein. In another aspect, X and G are a residue of hyaluronan.

Anti-Adhesion Composites

In one aspect, described herein are composites comprising (1) a first compound comprising a first anti-adhesion compound covalently bonded to a first anti-adhesion support and (2) a first prohealing compound. The term "anti-adhesion compound" as referred to herein, is defined as any compound that prevents cell attachment, cell spreading, cell growth, cell division, cell migration, or cell proliferation. In one aspect, compounds that induce apoptosis, arrest the cell cycle, inhibit cell division, and stop cell motility can be used as the anti-adhesion compound. Examples of anti-adhesion compounds include, but are not limited to anti-cancer drugs, anti-proliferative drugs, PKC inhibitors, ERK or MAPK inhibitors, cdc inhibitors, antimitotics such as colchicine or taxol, DNA intercalators such as adriamycin or camptothecin, or inhibitors of PI3 kinase such as wortmannin or LY294002. In one aspect, the anti-adhesion compound is a DNA-reactive compound such as mitomycin C. In another aspect, any of the oligonucleotides disclosed in U.S. Pat. No. 6,551,610, which is incorporated by reference in its entirety, can be used as the anti-adhesion compound. In another aspect, any of the anti-inflammatory drugs described below can be the anti-adhesion compound. Examples of anti-inflammatory compounds include, but are not limited to, methyl prednisone, low dose aspirin, medroxy progesterone acetate, and leuprolide acetate.

Representative Process for the Preparation of the Polymer Matrix:

A suspension of a solid form of a hydrophobic or poorly soluble bioactive agent is prepared in a water-based solution of a hydrophilic monomer or polymer. The active agents may be in the form of a solid, such as particles, microparticles, precipitates and the like. In certain aspect, the polymer formulation of the present application may be prepared as hydrogel polymer formulation as known in the art. In certain aspects, the hydrogel formulation of the present application provides a matrix composition that may be susceptible to certain enzymatic degradation processes, by hydrolytic degradation processes, or combinations thereof.

The polymer that may be employed in the process has the ability or may be subsequently converted or modified to have the ability or capacity to be crosslinked to form a three-dimensional crosslinked polymeric matrix containing occluded solid form of said bioactive agent. A number of well known biocompatible monomers, pre-polymers, polymers and their activated derivatives can be used in the present application as disclosed herein.

A variety of crosslinking chemical procedures can be used to form the polymeric matrix in vivo or for the manufacture of the polymers. Preferred crosslinking methods include, for example, reactions between electrophilic and nucleophilic functional groups, 1,4-conjugate additions or Michael addition reactions to an unsaturated carbon-carbon bonds, and radical chain reaction polymerization reactions. In addition the polymeric matrix can be formed by ionic (charge) crosslinking reactions, phase separation precipitation, aggregations, denaturation of polymers, complexation of complementary ligands (e.g., avidin/biotin, hapten/antibody, complementary nucleotide oligomers).

In certain aspect of the polymerization of the polymer of the present application, the polymerization process may be based on hydrophobic interactions, covalent bond formation, charge interactions, phase changes associated with thermo sensitive polymer compositions, denaturation processes, precipitations and various combinations thereof as is known in the art.

In one specific embodiment, we have incorporated solid form of steroid drugs into CARBYLAN-SX hydrogel, and the release of the steroid drugs were observed over time to provide a highly controlled, therapeutically effective release profile of the drugs.

In another embodiment, polymer composition of the present application comprising the bioactive agent may be employed in various methods of adhesion prevention and visco supplementation. See, for example, *The Journal of Rheumatology* 1993, vol. 20, Supplement 39, Viscosupplementation: A New Concept in the Treatment of Osteoarthritis; *J. Physiol.* 1953 119, 244-252, The Physiological Function of Hyaluronic Acid in Synovial Fluid; Viscous, Elastic and Lubricant Properties; Cooke et al., "The rheology of synovial fluid and some potential synthetic lubricants for degenerate synovial joints", pp. 66-72. Engineering in Medicine, vol. 7, No. 2, 1978; Gavrjushenko, "Recommendations with respect to the Improvement of lubricating qualities of synovial fluid in artificial joints", pp. 111-114. Part H: Hornal of Engineering in Medicine, Proc Instn Mech Engrs vol. 207, 1993.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Pharmaceutically Active Agents:

In one embodiment, there is provided a biodegradable polymer composition comprising a formulation for the administration of a hydrophobic pharmaceutically active agent. In one particular aspect, the pharmaceutically active agent are hydrophobic or the active agent may be made to be hydrophobic by chemical modification or derivatization using methods and derivatives well known to one skilled in the art. That is, the chemical derivatization may be the incorporation or the addition of hydrophobic groups to the active agent at a specific functional group of the active agent. Non-exclusive, representative functional groups amenable to derivatization include carboxyl groups, hydroxyl groups, amino groups, thiol groups, keto groups, and the like. The pharmaceutically active agent is in the form of solid particles, such as crystalline particles or in the amorphous solid forms.

In one embodiment, there is provided a biodegradable polymer composition comprising a hydrophobic pharmaceutically active agent selected from a drug, a vitamin, a nutritional supplement, a cosmeceutical or mixtures thereof.

In one embodiment, the hydrophobic pharmaceutically active agent is selected from the group consisting of antiinfectives such as antibiotics, anorexics, antiarthritics, antiasthmatic agents, anticonvulsants, antidepressants, antidiarrheals, antinauseants, antipruritics, antipsychotics, antipyretics, antispasmodics, anticholinergics, sympathomimetics, xanthine derivatives, cardiovascular preparations including calcium channel blockers and beta-blockers such as pindolol and antiarrhythmics; Diuretics; vasodilators including general coronary, peripheral and cerebral, central nervous system stimulants, cough and cold preparations, including decongestants, hormones such as estradiol and other steroids, including corticosteroids, hypnotics, immunosuppressives, muscle relaxants, parasympatholytics, psychostimulants, sedatives, and tranquilizers, and naturally derived or genetically engineered proteins, polysaccharides, glycoproteins or lipoproteins.

In another embodiment, the hydrophobic pharmaceutically active agent is selected from the group consisting of analgesics, anti-inflammatory agents, anthelmintics, anti-arrhythmic agents, anti-bacterial agents, anti-viral agents, anti-coagulants, antidepressants, anti-diabetics, anti-epileptics, anti-fungal agents, anti-gout agents, antihypertensive agents, anti-malarials, anti-migraine agents, anti-muscarinic agents, antineoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, antiparkinsonian agents, gastro-intestinal agents, histamine $H_1$ and $H_2$ receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, or mixtures thereof. In a particular aspect of the present application, the active agent is an anti-inflammatory agent. In another embodiment, the particular hydrophobic pharmaceutically active agent or drug is selected from the group consisting of Troxatyl®, fenofibrate, etoposide, aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenaminc acid, mefenamic acid, nabumetone, naproxen, oxaprozin, oxyphenbutazone, phenylbutazone, piroxicam, rofecoxib, sulindac, albuterol, alatrofloxacin, azithromycin, baclofen, benzathine penicillin, cinoxacin, ciprofloxacin HCl, clarithromycin, clofazimine, cloxacillin, demeclocycline, doxycycline, erythromycin, ethionamide, levofloxacin, lorefloxacin, moxifloxacin HCl, norfloxacin, ofloxacin, rifampicin, tetracycline, trimethoprim, trovafloxacin, vancomycin, amprenavir, delavirdine, efavirenz, indinavir, lamivudine, nelfinavir, nevirapine, ritonavir, saquinavir, stavudine, cilostazol, clopidogrel, ticlopidine, amoxapine, bupropion, fluoxetine HCl, maprotiline HCl, mianserin HCl, nortriptyline HCl, paroxetine HCl, sertraline HCl, trazodone HCl, carbamazepine, clonazepam, methylphenobarbitone, oxcarbazepine, paramethadione, phenobarbitone, phenyloin, butenafine HCl, butoconazole nitrate, fluconazole, ketoconazole, miconazole, sulconazole nitrate, terbinafine HCl, allopurinol, amlodipine, benidipine, benezepril, captopril, darodipine, dilitazem HCl, doxazosin HCl, enalapril, eposartan, losartan mesylate, lisinopril, minoxidil, nicardipine HCl, nifedipine, phenoxybenzamine HCl, prazosin HCl, reserpine, terazosin HCl, chloroquine, chlorproguanil HCl, halofantrine HCl, mefloquine HCl, quinine sulfate, dihydroergotamine mesylate, naratriptan HCl, sumatriptan succinate, atropine, capecitabine, chlorambucil, cyclosporin, ellipticine, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, carbimazole, chlormethiazole, chlorpromazine, chlorprothixene, clonazepam, clobazam, clotiazepam, clozapine, diazepam, droperidol, ethinamate, flunanisone, flunitrazepam, flurazepam, gabapentin, haloperidol, lorazepam, lormetazepam, methaqualone, methylphenidate, midazolam, molindone, nitrazepam, olanzapine, oxazepam, pentobarbitone, perphenazine pimozide, prochlorperazine, pseudoephedrine, alprenolol, atenolol, labetalol, metoprolol, nadolol, oxprenolol, pindolol, propranolol, aminone, digitoxin, digoxin, enoximone, lanatoside C, medigoxin, beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone, triamcinolone, acetazolamide, amiloride, metolazone, spironolactone, triamterene, pramipexole, ropinirole HCl, tolcapone, cimetidine, cisapride, diphenoxylate HCl, domperidone, famotidine, lanosprazole, loperamide, omeprazole, ondansetron HCL, ranitidine HCl, cetrizine, cyproheptadine HCl, flunarizine HCl, loratadine, meclizine HCl, oxatomide, terfenadine, calciprotriene, calcifediol, calcitriol, cholecalciferol, ergocalciferol, etretinate, retinoids, pravastatin, probucol, simvastatin, dantrolene sodium, tizanidine HCl, carotenes, dihydrotachysterol, essential fatty acids, non-essential fatty acids, phytonadiol, vitamin A, vitamin $B_2$, vitamin D, vitamin E, vitamin K, codeine, dextropropoxyphene, diamorphine, dihydrocodeine, fentanyl, meptazinol, methadone, morphine, nalbuphine, pentazocine, clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone, tibolone, amphetamine, dexamphetamine, raloxifene HCl, sibutramine HCl, sildenafil citrate, tacrine, tamsulosin HCl, and tolterodine.

In yet another embodiment, the pharmaceutically active agents, drugs or their salts that may be employed in accordance with the present application be selected from the following group of non-exclusive drugs: α-adregerngic agonists such as adrafinil, adrenalone, clonidine, cyclopentamine, detomidine, dimetofrine, dipivefrin, ephedrine, epinephrine, norepinephrine, norfenefrine, octodrine, octopamine, oxymetazoline, phenylephrine, phenylpropanolamine, phenylpropylmethylamine, pholedrine, propylhexedrine, seudoephedrine.

β-Adrenergic agonists such as formoterol, methoxyphenamine, ritodrine and terbuterol.

α-Adrenergic blocker such as dapiprazole, doxazosin, yohimbine.

α-Adrenergic blocker such as acebutolol, amosulalof, arotinolol, atenolol, bupranolol, carvedilol, epanolol, esmolol, levobunolol, mepindolol, metipranolol, metoprolol, moprolol, nadolol, nadoxolol, nifenalol, nipradilol, oxprenolol, penbutolol, pindolol, practolol and propranolol.

Anabolic such as androisoxazole, androstenediol, ethylestrenol, formyldienolone, 4-hydroxy-19-nortestosterone, methandriol, methenolone, methyltrienolone, nandrolone decanoate, stenbolone and trenbolone.

Analgesics such as alfentanil, allylprodine, alphaprodine, anileridine, benzylmorphine, bezitramide, buprenorphine, butorphanol, clonitazene, codeine, dihydrocodeine, fentanyl, hydrocodone, levorphanol, lofentanil, meperidine, meptazinol, methadone, morphine, morphine derivatives, myrophine, nalbuphine, nicomorphine, norlevorphanol, normethadone, normorphine, oxycodone, oxymorphone, sufentanil;

Analgesics such as acetaminophen, acetaminosalol, acetanilide, acetylsalicylates, acetylsalicylic acid, aceclofenac, alminoprofen, aloxiprin, aluminum bis(acetylsalicylate), aminochlorthenoxazin, 2-amino-4-picoline, aminopropylon, aminopyrine, antipyrine, antipyrin salicylate, antrafenine, apazone, aspirin, benorylate, etodolac, felbinac, fenoprofen, floctafenine, flufenamic acid, fluoresone, flupirtine, fluproquazone, flurbiprofen, ibufenac, imidazole salicylate, indomethacin, indoprofen, isofezolac, isoladol, isonixin, ketoprofen, ketorolac, p-lactophenetide, lefetamine, loxoprofen, methotrimeprazine, metofoline, miroprofen, morazone, morpholine salicylate, naproxen, nefopam, nifenazone, perisoxal, phenacetin, phenazopyridine, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metisulfate, salacetamide, salicin, salicylamide O-acetic acid, salicylic acid, salicylates and derivatives, salicylsulfuric acid, salsalate, salverine, simetride, sulfamipyrine, suprofen, talniflumate, tenoxicam, terofenamate, tetrandrine, tinoridine, tolfenamic acid, tolpronine, tramadol, viminol, xenbucin and zomepirac.

Androgen such as boldenone, fluoxymesterone, mestanolone, mesterolone, methandrostenolone, 17-methyltestosterone, 17α-methyl-testosterone 3-cyclopentyl enol ether, norethandrolone, normethandrone, oxandrolone, oxymetholone, prasterone, stanolone, stanozolol, testosterone, testosterone 17-chloral hemiacetal, testosterone 17-cypionate, testosterone enanthate, testosterone nicotinate, testosterone phenylacetate, testosterone propionate, tiomesterone.

Anesthetics such as acetamidoeugenol, alfadolone acetate, alfaxalone; ambucaine. amolanone, amylocalne, benoxinate, betoxycaine, biphenamine, bupivacaine, 2-chloroprocaine, cocaethylene, cocaine, ethyl aminobenzoate, ethyl chloride, etidocaine, etoxadrol, euprocin, fenalcomine, fomocaine, hexobarbital, hexylcaine, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencylidine, phenol, piperocaine, piridocaine, polidocanol, pramoxine, prilocalne, procaine, pseudococaine, pyrrocaine, risocaine, palicyl alcohol, tetracaine, thialbarbital, thiamylal and zolamine. Anorexic such as aminorex, amphecloral, benzphetamine, chlorphentermine, clobenzorax, cloforex, cyclexedrine, diphemethoxidine, fenbutrazate, fenfluramine, fenproporex, furfurylmethylamphetamine, levophacetoperane, mefenorex, metamfepramone, norpseudoephedrine, phenpentermine and picilorex. Antiallergics such as amlexanox, astemizole, azelastine, cromolyn, fenpiprane, histamine, ketotifen, nedocromil, oxatomide, pentigetide, repirinast, tiaramide, tranilast, traxanox, urushiol, cetirizine and fexofenadine.

Antianginals such as amlodipine, amyl nitrate, cinepazet maleate, imolamine, isosorbide dinitrate, limaprost, molsidomine, nitroxyalklamide derivatives. Antiarrhythmics such as adenosine, alprenolol, S-aminoalkyl-5-arylsulfoximines, amoproxan, aprindine, bretylium tosylate, bucumolol, bunaftine, butidrine, butobendine, capobenic acid, cifenline, disopyramide, encamide, flecamide, hydroquinidine, indecamide, ipratopium, lorajmine, lorcamide, meobentine, mexiletine, moricizine, pirmenol, prajmaline, procainamide, pronethalol, propafenone, pyrinoline, quinidine, quinidine sulfate, tocamide and viquidil. Antiarthritics/Antirheumatics such as allocupreide sodium, auranofin, aurothioglucose, aurothioglycamide, azathioprine, calcium 3-aurothio-2-propanol-1-sulfonate, clobuzarit, cuproxoline, diacerein, glucosamine, hydroxychloroquine, kebuzone, lobenzarit, melittin, myoral and penicillamine.

Antibiotic such as cefmetazole, cefazolin, cephalexin, cefoxitin, cephacetrile, cephaloglycin, cephaloridine; cephalosporins, such as cephalosporin c, cephalotin; cephamycins, such as cephamycin a, cephamycin b and cephamycin c, cepharin, cephradine, ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin.

Penicillins, such as penicillin n, penicillin o, penicillin s, and penicillin; chlorobutin penicillin; dicloxacillin; diphenicillin; heptylpenicillin, and metampicillin.

Macrolides such as azithromycin, carbomycin, clarithromycin, erythromycin and derivatives thereof, josamycin, leucomycins, midecamycins, miokamycin, oleandomycin, primycin, rosaramicin, roxithromycin, spiramycin, troleandomycin; tetracyclines such as apicycline, chlortetracycline, clomocycline, demeclocycline, guamecycline, lymecycline, meclocycline, methacycline, minocycline, oxytetracycline, penimepicycline, pipacycline, rolitetracycline, sancycline, senociclin, tetracycline nitrofurans such as furaltadone, furazolium, nifuradene, nifuratel, nifurfoline, nifurpirinol, nifurprazine, nifurtoinol; nitrofurantoin-quinolones and analogs such as amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, pfloxacin, pipemidic acid, piromidic acid, rosoxacin and temafloxacin.

Anticholinergic such as adiphenine, alverine, ambutonium, aminopentamide, amixetrine, amprotropine phosphate, anisotropine methylbromide, apoatropine, atropine, atropine n-oxide, benactyzine, benapryzine, benzetimide, benzilonium, benztropine mesylate, bevonium methyl sulfate; biperiden and butropium.

Anticonvulsant such as acetylpheneturide, albutoin, aloxidone, aminoglutethimide, 4-amino-3-hydroxybutyric acid, atrolactamide, beclamide, buramate, carbamazepine, cinromide, clonazepam, 3-methyl-5phenylhydantoin, narcobarbital, nimetazepam, nitrazepam, paramethadione, phenacemide, pheneturide, phensuximide, phenyloin, phethenylate sodium, primidone, progabide, solanum, strontium, suclofenide, sulthiame, tetrantoin, trimethadione, valproic acid, valpromide, vigabatrin and zonisamide.

Antidepressants such as binedaline, caroxazone, citalopram, dimethazan, indalpine, fencamine, indeloxazine, nefopam, nomifensine, oxitriptan, oxypertine, paroxetine, sertraline, thiazesim, trazodone, zometapine; Hydrazides/ hydrazines such as benmoxine, iproclozide, iproniazid, isocarboxazid, nialamide, octamoxine, pheneizine; Pyrrolidones such as cotinine, rolicyprine and rolipram.

Tetracyclics such as maprotiline, metralindole, mianserin, oxaprotiline. tricyclics such as adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine n-oxide, iprindole, lofepramine, melitracen, metapramine, nortriptyline, noxiptilin, opipramol, propizepine, protriptyline, quinupramine, tianeptine, trimipramine. Others such as benactyzine, bupropion, butacetin, deanol, deanol aceglumate, deanol acetamidobenzoate, dioxadrol, etoperidone, febarbamate, femoxetine, fenpentadiol, fluoxetine, fluvoxamine, hematoporphyrin, hypericin, levophacetoperane, lithium medifoxamine, minaprine, moclobemide, oxaflozane, piberaline, polycyclic imides, prolintane, pyrisuccideanol, rubidium, sulpiride, sultopride, teniloxazine, thozalinone, tofenacin, toloxatone, tranylcypromine, 1-tryptophan, viloxazine and zimeldine.

Antidiabetic biguanides such as buformine, metformin, phenformin; sulfonylurea derivatives such as acetohexamide, 1-butyl-3-metanilylurea, carbutamide. chlorpropamide, glibornuride, gliclazide, glipizide, gliquidone, glisoxepid, glyburide, glybuthiazole, glybuzole, glyhexamide, glymidine, giypinamide, phenbutamide, tolazamide, tolbutamide and tolcyclamide.

Antidiarrheal such as acetyltannic acid, albumin tannate, alkofanone, aluminium salicylates, catechin, difenoxin, diphenoxylate, lidamidine, loperamide, mebiquine, trillium, uzarin.

Antidiuretic such as desmopressin, felypressin, lypressin, ornipressin, oxycinchophen, terlipressin and vasopressin.

Antifungal (antibiotics) polyenes such as amphotericin-b, candicidin, dermostatin, filipin, fungichromin, hachimycin, hamycin, lucensomycin, mepartricin, natamycin, nystatin, pecilocin and perimycin.

Antihypertensive; benzothiadiazine derivatives such as althiazide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethiazide, methyclothiazide, meticrane, metolazone, paraflutizide, polythiazide, tetrachlormethiazide and trichlormethiazide.

Antihyperthyroid such as 2-amino-4-methylthiazole, 2-aminothiazole, carbimazole, 3,5-dibromo-1-tyrosine, 3,5-diiodotyrosine, hinderin, iodine, lothiouracil, methimazole, methylthiouracil, propylthiouracil, sodium perchlorate, thibenzazoline, thiobarbital and 2-thiouracil.

Nonsteroidal anti-inflammatory such as aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, and tolmetin; thiazinecarboxamides such as droxicam, isoxicam and piroxicam.

Antimalarials such as acedapsone, alphaminoquinolines, aminoquinolines, amodiaquin, arteether, artemether, artemisinin, artesunate, bebeerine, chirata, chlorguamide, chloroquine, chlorproguanil, chinchona, cinchonidine, cinchonine, cycloguanil, euqinine, gentiopicrin, halofantrine, mefloquine hydrochloride, 3-methylarsacetin, pamaquine, plasmocid, primaquine, pyrimethamine, quinacrine, quinine, (acids, salts and derivatives), quinine formate, quinine gluconate, quinine tannate, quinine urea hydrochloride, quinocide, quinoform, quinoline, sodium arsenate and diabasic.

Antimigraine such as alpipropide, dihydroergotamine, ergocornine, ergocorninine, ergocryptine, ergot, ergotamine, flumedroxone flumedroxone acetate, fonazine, methysergide, oxetorone, pizotyline and sumatriptan.

Antinauseant such as acetylleucine monoethanolamine, bietanautine, bromopride, buclizine, clebopride, cyclizine, dimenhydrinate, diphenidol, domperidone, granisetron, meclizine, methallatal, metoclopramide, metopimazine, nabilone, ondansetron, oxypendyl, pipamazine, piprinhydrinate, scopolamine, tetrahydrocannabinols, thiethylperazine and trimethobenzamide.

Antineoplastic; alkyl agents: alkyl sulfonates such as busulfan, improsulfan, piposulfan, aziridines such as benzodepa, carboquone, meturedepa, uredepa; Ethylenimines and methylmelamines such as altretamine, triethylenemelamine, triethylenephosphoramide, triethylenethiophosphoramide and trimethylolmelamine. Antibiotics such as aclacinomycins, actinomycin, anthramycin, azaserine, bleomycins, cactinomycin, carubicin, carzinophilin, chromomycins, dactinomycin, daunorubicin, carzinophilin, chromomycins, dactinomycin, daunorubicin, 6-diazo-5oxo-1-norleucine, doxorubicin, epirubicin, mitomycins, mycophenolic acid, nogalamycin, olivomycins, peplomycin, plicamycin, profiromycin, puromycin, streptonigrin, streptozocin, tubercidin, ubenimex, zinostatin and zorubicin.

Antiparkinsonian such as amantadine, benserazide, bietanautine, biperiden. budipine, carbidopa, deprenyl, dexetimide, diethazine, droxidopa, ethopropazine, ethylbenzhydramine, levodopa, piroheptine, pridinol, prodipine, terguride, tiapride and tigloidine.

Antipsychotic; butyrophenones such as benperidol, bromperidol, droperidol, fluanisone, haloperidol, melperone, moperone, pipamperone, spiperone, timiperone, trifulperidol; phenothiazines such as acetophenazine, butaperazine, carphenazine, chlorproethiazine, chlorpromazine, clospirazine, mepazine, mesoridazine, methoxypromazine, metofenazate, oxflumazine, perazine, pericyazine, perimethazine, prochlorperazine, promazine, sulforidazine, thiopropazate, thioridazine, trifluoperazine, triflupromazine; thioxanthenes such as chlorprothixene, clopenthixol, flupentixol and thiothixene.

Antispasmodic such as alibendol, ambucetamide, aminopromazine, bietamiverine, butaverine, butropium, caroverine, cimetropium, cinnamedrine, clebopride, properidine and propivane.

Antiulcerative such as aceglutamide aluminum complex, acetamidocaproic acid zinc salt, acetoxolone, arbaprostil, benexate hydrochloride, bismuth subcitrate, carbenoxolone, cetraxate, cimetidine, enprostii, esaprazole, famotidine, ftaxilide, gefarnate, guaiazulene, irsogladine, nizatidine, omeprazole, omoprostil, yoryzanol, pifamine, pirenzepine, plaunotol, ranitidine, trimoprostil, trithiozine, troxipide and olimidine.

Antiviral; purines/pyrimidines such as 2-acetyl-pyridine 5-((2-pyridylamino)thiocarbonyl), thiocarbonohydrazone, acyclovir, dideoxyadenosine, dideoxycytidine, dideoxyinosine, edoxudine, floxuridine, ganciclovir, idoxuridine, pyridinon, trifluridine, vidarabine and zidovudine.

Anxiolytic; Arylpiperazines such as buspirone, gepirone, ipsapirone; benzodiazepine derivatives alprazolam, bromazepam, camazepam, chlordiazepoxide, clobazam, clorazepate, clotiazepam, cloxazolam, diazepam, ethyl loflazepate, etizolam, fluidazepam, flutazolam, flutoprazepam, halazepam, ketazolam, lorazepam, loxapine, medazepam, metaclazepam, mexazolam, nordazepam, oxazepam, oxazolam, pinazepam, prazepam and tofisopam.

Calcium channel blocker; Arylalkylamines such as bepridil, diltiazem, fendiline, gallopamil, terodiline, verapamil.

Cardiotonic such as acetyldigitoxins, 2-amino 4-picoline, aminone, buclasdesine, cerberoside, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, lanatosides and metamivam.

Cholinergic such as aceclidine, acetylcholine bromide, acetylcholide, aclatonium napadisilate, benzpyrinium bromide, bethanechol, carbachol, carpronium, demecarium, dexpanthenol, diisopropyl paraoxon, echothiophate, edrophonium, eseridine, furtrethonium, isofluorophate, methacholine chloride, muscarine neostigmine, oxapropanium, physostigmine and pyridostigmine.

Cholinesterase inhibitor such as ambenonium, distigmine and galanthamine. Steroids such as canrenone, oleandrin, spironolactone; sulfonamide derivatives such as acetazolamide, azosemide, bumetanide, butazolamide, chloraminophenamide, clofenamide, clorexolone, diphenylmethane-4,4'-disulfonamide, disulfamide, ethoxzolamide, flumethiazide, mefruside, methazolamide and piretamide torasemide, Glucocorticoid such as 21-acetoxypregnenolone, alclometasone, algestone, amcinonide, beclomethasone, betamethasone, betamethasone dipropionate, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, formocortal, halcinonide, halometasone, halopredone acetate, hydrocotramate, hydrocortisone, hydrocortisone acetate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diethylaminoacetate, prednisolone sodium succinate, prednisolone sodium phosphate, prednisolone sodium 21-sulfobenzoate, prednisolone 21-stearoylglycolate, prednisolone tebutate, prednisolone 21-trimethylacetate, prednisone, prednival, prednylidene, prednylidene 21-diethylaminoacetate, tixocortal, triamcinolone, triamcinolone acetonide, triamcinolone benetonide and triamcinolone hexacetonide. Gonad stimulating agents such as clomiphene, cyclofenil, epimestrol, FSH, HCG and LH-RH.

Gonadotropic hormone such as LH, PMSG growth hormone inhibitor such as somatostatin; growth hormone releasing factor such as sermorelin; growth stimulant such as somatotropin.

Immunosuppressant such as cyclophilin, cyclosporins, FK-506, mizoribine, rapamycin, rapamycin sulfamates.

LH-RH agonist such as buserelin, goserelin, leuprolide, nafarelin, triptorelin. Muscle relaxant (skeletal) such as afloqualone, alcuronium, atracurium besylate, baclofen, benzoquinonium, c-calebassine, carisoprodol, chlorphenesin carbamate, chlorzoxazone, curare, cyclobenzaprine, dantrolene, decamethonium, eperisone, fazadinium, flumetramide, gallamine triethiodide, hexacarbacholine, hexafluorenium, idrocilamide, laudexium methyl sulfate, leptodactyline, memantine, mephenesin, metaxalone, methocarbamol, metocurine iodide, pancuronium, pipecurium, promoxolane, quinine sulfate, styramate, succinylcholine, succinylcholine suxethonium bromide, tetrazepam, thiocolchicoside, tizanidine, tolperisone, tubocurarine, vecuronium and zoxazolamine.

Steroids such as betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, triamcinolone, norethindrone, norethindrone acetate, norethynodrel, norgesterone, norgestimate, norgestrel, norgestrienone, 19-norprogesterone, norvinisterone, pentagestrone, progesterone, promegestone, quingestrone and trengestone.

There are large numbers of pharmaceutically active agents or drug substances that are very slightly or practically insoluble in water. According to the U.S. Pharmacopeia (U.S.P.) XXI (page 1441) a drug substance is described as 'very slightly soluble' if one part of solute (drug substance) requires from 1,000-10,000 parts of solvent to dissolve it and as 'practically insoluble' if one part of solute requires more than 10,000 parts of solvent to dissolve it or its solubility is less than 0.1 mg/ml of solvent. In the reference tables on the approximate solubility of various drug substances provided on pages 1483-1490 of U.S.P. XXI there is provided a list of a number of drugs that are "very slightly soluble" or "practically insoluble" in water. In addition, of the biologically active agents described above, those agents that are water soluble may be rendered insoluble or relatively water insoluble by converting the agents to a water insoluble derivative or a water insoluble salt as known in the art.

In another aspect, the biologically active agent may also be selected from biologically active peptides, growth factors, and nucleic acid constructs as known in the art. In cases where the active agents are sufficiently basic or acidic to form stable nontoxic acid or base salts, administration of the agents are performed as their salts. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including, sulfate, nitrate, bicarbonate and carbonate salts. Pharmaceutically acceptable salts may be obtained using standard procedures well known in the art, for example, by reacting a sufficiently basic compound such as an amine with a suitable acid affording a physiologically acceptable anion. Alkali metal (such as sodium, potassium or lithium) or alkaline earth metal (e.g. calcium) salts of carboxylic acids may be prepared. Suitable pharmaceuticals for parenteral administration are well known as is exemplified by the *Handbook on Injectable Drugs,* 6th edition, by Lawrence A. Trissel, American Society of Hospital Pharmacists, Bethesda, Md., 1990.

Any of the compounds, compositions, and composites described herein can be the pharmaceutically acceptable salt or ester thereof if they possess groups that are capable of being coverted to a salt or ester. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine and the like.

In one embodiment, the composition further comprises one or more prohealing compounds. The term "prohealing drug" as defined herein is any compound that promotes cell growth, cell proliferation, cell migration, cell motility, cell adhesion or cell differentiation. In one aspect, the prohealing compound includes a protein or synthetic polymer. Proteins useful in the methods described herein include, but are not limited to, an extracellular matrix protein, a chemically-modified extracellular matrix protein, or a partially hydrolyzed derivative of an extracellular matrix protein. The proteins may be naturally occurring or recombinant polypeptides possessing a cell interactive domain. The protein can also be mixtures of proteins, where one or more of the proteins are modified. Specific examples of proteins include, but are not limited to, collagen, gelatin, elastin, decorin, laminin, or fibronectin, vitronectin, alpha-2 macroglobulin, chondromodulin, aggrecan, link protein, cartilage oligomeric protein and lubricin.

In one aspect, the synthetic polymer has at least one carboxylic acid group or the salt or ester thereof, which is capable of reacting with a hydrazide or an aminoooxy ether compound. In one aspect, the synthetic polymer comprises glucuronic acid, polyacrylic acid, polyaspartic acid, polytartaric acid, polyglutamic acid or polyfumaric acid.

In another aspect, the prohealing compound can be any of the supports disclosed in U.S. Pat. No. 6,548,081 B2, which is incorporated by reference in its entirety. In one aspect, the prohealing compound includes cross-linked alginates, gelatin, collagen, cross-linked collagen, collagen derivatives, such as, succinylated collagen or methylated collagen, cross-linked hyaluronan, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(L-glutamic acid), poly(D-glutamic acid), polyacrylic acid, poly(DL-glutamic acid), poly(L-aspartic acid), poly(D-aspartic acid), poly(DL-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin. In another aspect, highly cross-linked HA can be the prohealing compound.

In another aspect, the prohealing compound can be a polysaccharide. In one aspect, the polysaccharide has at least one group, such as a carboxylic acid group or the salt or ester thereof that can react with a dihydrazide. In one aspect, the polysaccharide is a glycosaminoglycan (GAG). Any of the glycosaminoglycans described above can be used in this aspect. In another aspect, the prohealing compound is hyaluronan.

In one embodiment, the compounds used for this invention are polysaccharides that have a free thiol functional group. The free thiol can be linked to the polysaccharide via a hydrazide linkage. Specific polysaccharides that can be used include but are not limited to chondroitin sulfate, dextran, dermatan, heparan, heparin, dermatan sulfate, heparan sulfate, alginic acid, pectin, chitosan, hyaluronic acid or carboxymethylcellulose. Specific examples of these types of polymers are described in WO 05/056608, U.S. Pat. No. 5,874,417 and U.S. patent application 20050176620. Specific examples of these functionalized polysaccharides are shown in structures X1 to X3.

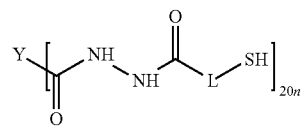

$n \geq 2$; $L$—$(CH_2)n$- where $1 \leq n \geq 20$;
Y=polysaccharide

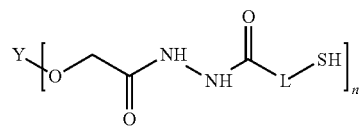

$n \geq 2$; $L$—$(CH_2)n$- where $1 \leq n \geq 20$;
Y=polysaccharide

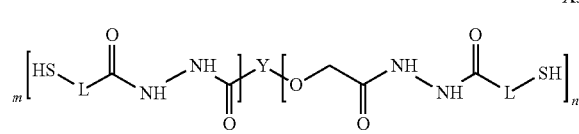

$n \geq 2$, $m \geq 2$; $L$—$(CH_2)n$-, where $1 \leq n \geq 20$; Y=polysaccharide.

In one embodiment the thiol functionalized polysaccharide can be hyaluronic acid. Specific examples of functionalized hyaluronic acid are shown in structures X4 to X6.

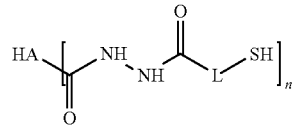

Structure X4 where $n \geq 2$, $L$—$(CH_2)_n$— where $1 \leq n \geq 20$ and HA=hyaluronic acid where the group is attached through the carboxylic acid of the glucuronic acid unit

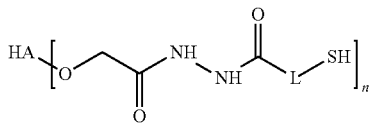

where $n \geq 2$, $L$—$(CH_2)_n$— where $1 \leq n \geq 20$, and HA=hyaluronic acid where the group is attached through the 6-hydroxy group of the N-acetyl glucosamine unit

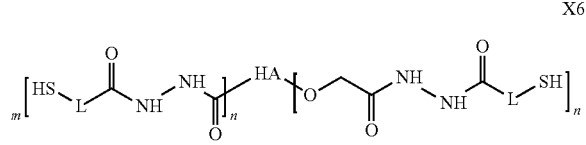

where $n \geq 2$, $m \geq 2$, $L$—$(CH_2)_n$— where $1 \leq n \geq 20$; HA=hyaluronic acid where the ether linkage is through the 6-hydroxy group of the N-acetyl glucosamine unit and the —CO—NH—NH—CO-L-SH linkage is through the carboxylic acid of the glucuronic acid unit. In one embodiment L is —CH$_2$—CH$_2$— in structures 4 to 6. Examples of these structures are shown in structures 7 to 9.

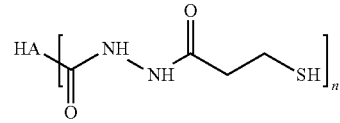

X7 where n≥2 and HA=hyaluronic acid where the group is attached through the carboxylic acid of the glucuronic acid unit

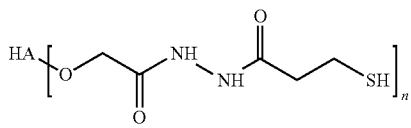

X8 where n≥2 and HA=hyaluronic acid where the group is attached through the 6-hydroxy group of the N-acetyl glucosamine unit.

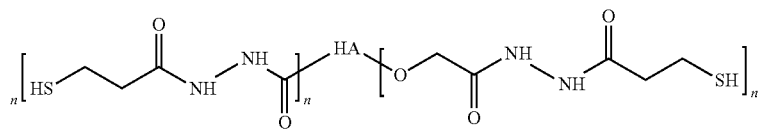

X9 where n≥2, m≥2; and HA=hyaluronic acid where the ether linkage is through the 6-hydroxy group of the N-acetyl glucosamine unit and the —CO—NH—NH—CO—CH$_2$—CH$_2$—SH linkage is through the carboxylic acid of the glucuronic acid unit.

In another embodiment, the hyaluronic acid derivative used for this invention can be a hyaluronic acid derivative that has been obtained through the reaction of a biscarbodimide functionalized molecule with the glucuronic acid units of hyauronic acid. These hyaluronic acid derivatives have an N-acyl urea group that links the core of the biscarbodiimide molecule to the hyaluronic acid. Biscarbodiimide compounds that can be used include compounds represented by the structures 1, 2 and 3.

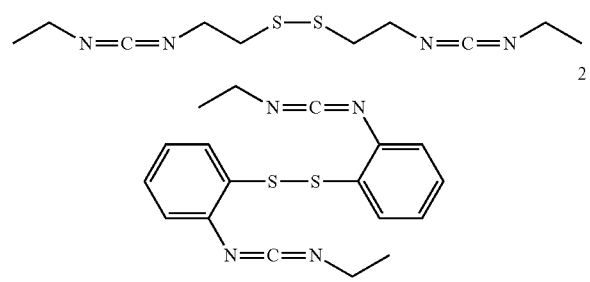

1

2

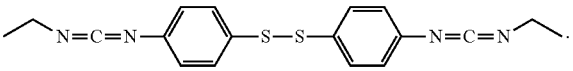

3

Specific examples of such materials are described in U.S. Pat. Nos. 5,502,081, 6,013,679, 6,548,081, 6,620,927, and 6,884,788 and U.S. patent applications 20020128512, 20040038934 and 20050136122. In another embodiment, the hyaluronic acid derivative used in the present invention can include hyaluronic acic that is funtionalized with one or more free thiol groups which can then undergo (1) an oxidation reaction to form a disulfide bond such that a crosslinked material is obtained and/or (2) can react with a homofunctional or heterofunctional crosslinker that has 2 or more thiol reactive groups (e.g. allyl, acrylate, methacrylate, maleimide, n-hydroxysuccimdyl, haloalkyl groups (e.g., iodoacetyl functions) etc). In one embodiment, examples of such thiol functionalized HA derivatives include hyalyronic that has been functionalized with a biscarbodiimide having an intramolecular disulfide bond that has then been subsequently reacted with a reducing agent to reduce the disulfide bond to free thiol groups. These thiol functionalized hyaluronic acid derivatives have at least one pendant thiol group that is linked to the hyaluronic acid through an N-acyl urea group. This pendant thiol group can be linked to the N-acyl urea group through a hydrocarbyl, aryl, substituted-hydrocarbyl, or substituted aryl group. Examples of these types of thiol functionalized hyaluronic acid derivatives are shown by structures 4 to 6.

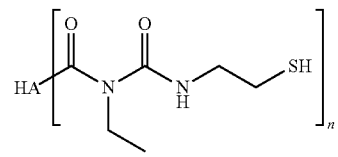

4

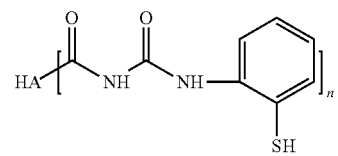

5

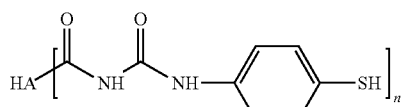

6 wherein for each of the above structures, n≥2.

Specific examples of these thiol functionalized hyaluronic acids are described in U.S. Pat. No. 6,884,788 and U.S. patent applications 20020128512, 20040038934 and 20050222083. In another embodiment, the thiol functionalized hyaluronic acid derivative can be prepared, as described by HA. R. V. Sparer et al., 1983, Chapter 6, pages 107-119, in T. J. Roseman et al., Controlled Release Delivery Systems, Marcel Dekker, Inc., New York, in which hyalyronic acid was modified by attaching cysteine residues to the HA via amide bonds. In another embodiment, the thiol functionalized hyaluronic acid can be represented by structure 5, which is described in PCT/US2007/073291.

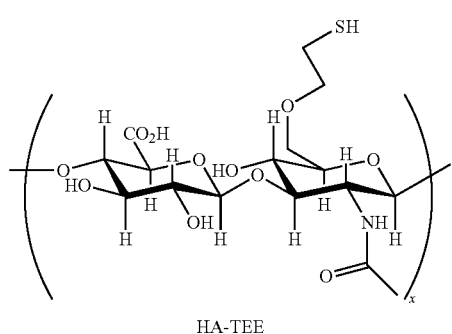

HA-TEE

In another embodiment, the thiol functionalized hyaluronic acid can be represented by structure 6 or 7.

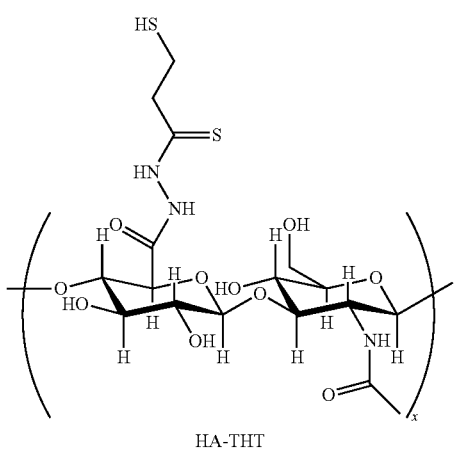

HA-THT

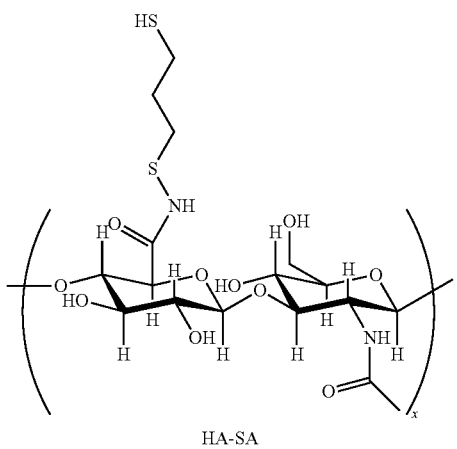

HA-SA

In another embodiment, the hyaluronic acid derivatives that can be used are an aldehyde functionalized hyaluronic acid which can react with an amine functionalized hyaluronic acid or a hydrizide-functionalized hyaluronic acid to produce a crosslinked matrix. Specific examples of aldehyde functionalized hyaluronic acid that can be used are shown in structures 8 and 9, wherein for each of the above structures, $n \geq 2$.

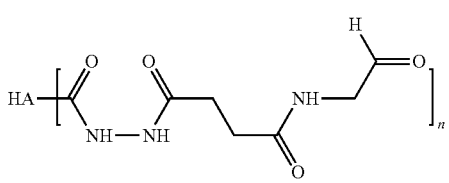

Specific examples of amine-functionalized hyaluronic acid that can be used are shown in structures 10 to 14.

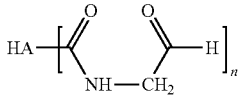

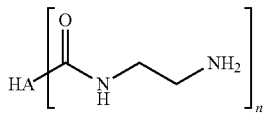

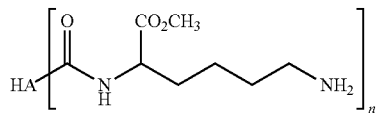

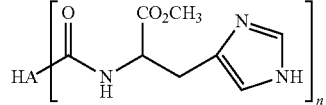

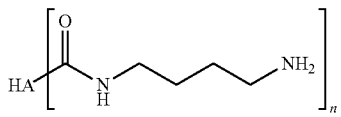

wherein for each of the above structures, $n \geq 2$.

The synthesis of structures 8 to 14 are described in U.S. Pat. Nos. 6,630,457 and 7,196,180. In yet another embodiment the in-situ forming material can be formed by the reaction of an amine functionalized hyaluronic acid and a hyaluronic acid that contains an activated ester group. Examples of specific amines that can be used are shown in structures 10 to 14. Examples of specific hyaluronic acid derivatives that contain activated esters are shown in structures 15 to 17.

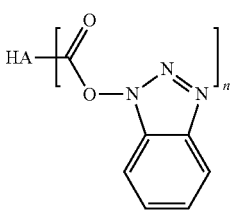

-continued

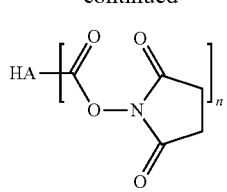

16

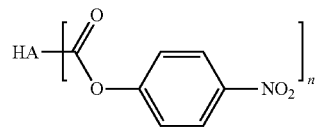

17 wherein for each of the above structures, n≥2.

In each of the compounds disclosed herein, m and n may be independently ≥2, and less than about 15,000. In certain variation, m and n may be independently less than about 13,000, less than 12,000, less than 10,000, less than 8,000, less than 7,000, less than 5,000, less than 3,000, less than 2,000, less than 1,000, less than 500 or less than about 100.

In yet another embodiment, the hyaluronic acid that is derivatized with nucleophilic group can be reacted with non-hyaluronic acid polymers or small molecule crosslinkers that are derivatized with electrophilic groups. Examples of specific hyaluronic acid derivatives that contain a nucleophilic group are shown in structures 10 to 14. Examples of polymers or small molecule crosslinkers containing electrophilic groups include polymers or small molecules that have allyl, vinyl, acrylate, methacrylate, and/or activated esters. A specific example of such a polymer includes a polyethylene glycol (PEG) polymer which has been functionalized with a succinimidyl group. An example of such a polymer is shown in structure 18.

18

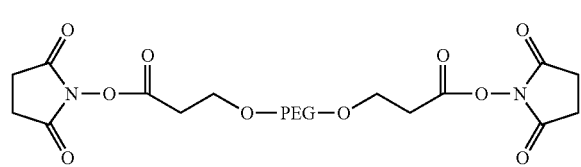

A specific example of an electrophilic funtionalized small molecule is shown in structure 19.

19

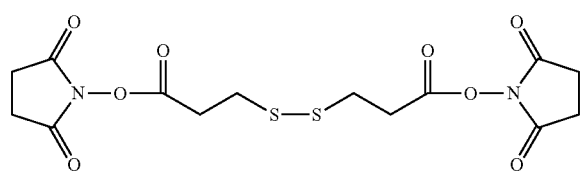

The composite can optionally contain a second prohealing compound. In one aspect, the second prohealing compound can be a growth factor. Any substance or metabolic precursor which is capable of promoting growth and survival of cells and tissues or augmenting the functioning of cells is useful as a growth factor. Examples of growth factors include, but are not limited to, a nerve growth promoting substance such as a ganglioside, a nerve growth factor or neuropeptides (Substance P, Calcitonin Gene Related Peptide, Vasoactive Intestinal Peptide), and the like; a hard or soft tissue growth promoting agent such as fibronectin (FN), human growth hormone (HGH), insulin, a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF-1 and 2, FGF-18), interleukin-1 receptor antagonists (IL-1RA), vascular endothelial growth factor (VEGF) and keratinocyte growth factor (KGF), demineralized bone material, CXC cytokines, Nexins, members of the Wnt family of proteins, Decoy receptor 3 protein (DcR3), and the like; and antineoplastic agents such as methotrexate, 5-fluorouracil, adriamycin, vinblastine, cisplatin, tumor-specific antibodies conjugated to toxins, tumor necrosis factor, and the like. The amount of growth factor incorporated into the composite will vary depending upon the growth factor and prohealing compound selected as well as the intended end-use of the composite.

Any of the growth factors disclosed in U.S. Pat. No. 6,534, 591 B2, which is incorporated by reference in its entirety, can be used in this aspect. In one aspect, the growth factor includes transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin and insulin-like growth factor (IGF)); inhibins (for example, Inhibin A, Inhibin B); growth differentiating factors (for example, GDF-5, 6 and 7); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, monomeric forms, or derivatives of these factors can be used, provided that they exhibit at least some of the biological activity of the native molecule. For example, analogs can be prepared by expression of genes altered by site-specific mutagenesis or other genetic engineering techniques.

In another aspect, the addition of a crosslinker can be used to couple the first compound with the prohealing compound. In one aspect, when the first compound and the prohealing compound possess free thiol groups, a crosslinker having at least two thiol-reactive electrophilic groups can be used to couple the two compounds. Additionally, the crosslinker can couple two first compounds or two prohealing compounds.

In another embodiment, the pharmaceutically active agent can be an agent that is osteogenic, osteoconductive and/or osteoinductive. Examples of these agents include, but are not limited to the LIM mineralization proteins (LMPs), osteogenic proteins (e.g., OP-1, OP-2, or OP-3), demineralized bone matrix (DBM) calcium sulfate and calcium phosphate.

In one embodiment, the pharmaceutically active agent can be calcium sulfate. In one embodiment, the calcium sulfate is selected from the group consisting of alpha-calcium sulfate hemihydrate, beta.-calcium sulfate hemihydrate, calcium sulfate dihydrate, and mixtures thereof.

In another embodiment, the pharmaceutically active agent can be calcium phosphate. In one embodiment, the calcium phosphate is selected from the group consisting of hydroxyapatite, tricalcium phosphate, tetracalcium phosphate, anhydrous dicalcium phosphate, monocalcium phosphate monohydrate, dicalcium phosphate dihydrate, heptacalcium phosphate, octocalcium phosphate, calcium pyrophosphate, oxyapatite, calcium metaphosphate, carbonatoapatite, dahlite, and combinations thereof.

In one embodiment, the calcium phosphate is alpha-tricalcium phosphate, beta-tricalcium phosphate, and combinations thereof. In one embodiment, the calcium phosphate composition can comprise about 17 to about 42 percent alpha-tricalcium phosphate and about 58 to about 83 percent beta-tricalcium phosphate.

Particle Size and Size Distributions:

In one embodiment, the particle size of the drugs or biologically active agents that may be used in the present application is about 10 nanometers to 500 microns, or about 1 micron to about 250 microns. In certain aspects, the particle size of the drug or agent is preferably about 10 microns to 20 microns. The particle size may be based on sieving limitations and the anticipated cellular (macrophage) uptake. In another embodiment, the particle size of the drugs or biologically active agents that may be used in the present application is about 500 microns to about 1000 microns, or about 1000 microns to about 2000 microns. In a particular variation, the particles are between 0.01 microns and 2000 microns. In another variation, the particles are between about 0.01 microns and 100 microns, between 100 microns and 200 microns, between 200 microns and 300 microns, between 300 microns and 400 microns, and between 400 microns and 500 microns. In certain variations, the particles are between about 500 microns and 600 microns, between 600 microns and 700 microns, between 700 microns and 800 microns, between 800 microns and 900 microns, between 900 microns and 1000 microns, between 1000 microns and 1100 microns, between 1100 microns and 1200 microns, between 1200 microns and 1300 microns, between 1300 microns and 1400 microns, between 1400 microns and 1500 microns, between 1500 microns and 1600 microns, and between 1600 microns and 1700 microns. In particular variations, the particles are between 1700 microns and 1800 microns, between 1800 microns and 1900 microns, between 1900 microns and 2000 microns. In certain variations, the particles are between about 1 micron and 1900 microns, between 100 microns and 1800 microns, between 200 microns and 1700 microns, between 300 microns and 1600 microns, between 400 microns and 1500 microns, between 500 microns and 1400 microns, between 600 microns and 1300 microns, between 700 microns and 1200 microns, and between 800 microns and 1100 microns.

Parenteral administration of a composition of the invention can be affected by either subcutaneous or intramuscular injection. Parenteral formulations of the copolymer may be formulated by mixing one or more therapeutic agents with a liquid copolymer. The therapeutic agent may be present as a finely divided solid, or any other appropriate particles, solid or crystalline physical form. Optionally, the compositions include one or more parenteral additives, e.g., nontoxic auxiliary substances such as diluents, carriers, excipients, stabilizers or the like. Other suitable parenteral additives may be formulated with the copolymer and pharmaceutically active agent or compound, however, if water is to be used it should be added immediately before administration.

Excipients:

In one aspect of the present invention, the compositions of the invention can further comprise one or more excipients. These excipients can be pharmaceutically acceptable excipients. Such excipients include, but are not limited to freeze-drying agents, agents that modulate pH, agents that modulate osmolality of the product, agents that enhance or retard product solubility, stabilizers, free radical scavengers, anti-oxidants, other useful agents known to those of skill in the art or combinations of two or more of excipients. Known useful agents include, but are not limited to polyethylene glycol (PEG), dextran, dithiothreitol (DTT), ascorbic acid and ethylenediamine tetraacetic acid (EDTA). Freeze-drying agents aid in stabilizing against the rigors of freeze-drying or storage at subzero temperatures. Illustrative examples of freeze drying agents include, but are not limited to a sugar or an amino compound. Such agents may include mannitol, glucose, sucrose, lactose, maltose, and trehalose; polysaccharides, such as dextrose, dextrins, and cyclodextrins; nonnatural polymers, such as polyvinylpyrrolidone (PVP); and amino acids as disclosed in U.S. Pat. No. 5,472,706.

Illustrative examples of stabilizers include, but are not limited to, the following: fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalosel amino acids, such as histidine, N-acetylcysteine (NAC), glutamic acid, tryptophan, sodium carpryl N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and cysteine; trace elements, such as selenium; vitamins, such as vitamin A, vitamin C or ascorbic acid (including its derivatives and salts such as sodium ascorbate and palmitoyl ascorbic acid) and vitamin E (and its derivatives and salts such as tocopherol acetate, d-alpha tocopheryl polyethylene glycol 1000 succinate, and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citilone; puercetin; chrysin: dimethyl sulfoxide (DMSO); piperazine diethanesulfonic acid (PIPES); imidazole; methoxypsoralen (MOPS): 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthacyanidins; ammonium sulfate; Pegorgotein (PEG-SOD); N-tert-butyl-alpha-phenylnitrone (PEN); o-vanillin (3-methoxysalicylaldehyde) and 4-hydroxy-2,2,6,6-tetramethylpiperidin-1-oxyl (Tempol).

Some chemical compounds act as scavengers for one or more reactive species generated during sterilization, particularly irradiation. Examples of scavenger compounds useful in this application include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a beta-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom. Bisulfites and sulfites useful as the formaldehyde scavenger compound in this application include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like. Examples of amines useful in this application include the aliphatic and aromatic amines such as, for example, aniline, benzidine, aminopyrimidine, toluene-diamine, triethylenediamine, diphenylamine, diaminodiphenylamine, hydrazine, and hydrazide. Suitable amides for use in this application include urea, cyanamide, acrylamide, benzamide and acetamide. Suitable alcohols include phenols, 1,4-butanediol, d-sorbitol and polyvinyl alcohol. Examples of suitable compounds having a beta-dicarbonyl group include malonic acid, acetylacetone, ethylacetone, acetate, malonamide, diethylmalonate or another malonic ester. Cyclic ketones suitable for use in this application include cyclohexanone or cyclopentanone.

Examples of suitable heterocyclic compounds for use as a scavenger in this application are disclosed, for example, in U.S. Pat. No. 4,127,382. Such heterocyclic compounds include, for example, benzimidazole, 5-methyl benzimidazole, 2-methylbenzimidazole, indole, pyrrole, 1,2,4-triazole, indoline, benzotriazole, indoline and the like.

Preservatives:

In one aspect of the present invention, preservatives are included in the composition. The preservative may be selected from among anti-microbial agents, parabens, cresols, metal compounds and other known agents. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservative may be selected from known antimicrobial metal compounds or elemental metals including, but not limited to, mercurial compounds, such as phenolmercuric chloride, phenolmercuric acetate, acetomeroctol, nitromersol, thimerosal, mercurochrome, mercuric chloride, and mercuric iodide; elemental metals, such as silver and copper; and metal compounds, such as copper chloride, copper sulfate, copper peptides, zinc chloride, zinc sulfate, silver nitrate, silver iodide, silver acetate, silver benzoate, silver carbonate, silver chloride, silver citrate, silver oxide, silver sulfate and tincture of iodine. Further information on antimicrobial activities of metals can be found, for example, in S. Seymour Block, DISINFECTION, STERILIZATION AND PRESERVATION, 5$^{th}$ Ed., Philadelphia: Lippincott Williams & Wilkins, 2000. The preservative can also be selected from other known agents including, but not limited to, hydroquinone, pyrocatechol, resorcinol, 4-n-hexyl resorcinol, 3☐,4,7,7☐-tetrahydro-2-((trichloromethyl)thio)-1H-isoindole-1,3(2H)-dione, benzalkonium chloride, benzalkonium chloride solution, benzethonium chloride, benzoic acid, benzyl alcohol, cetylpyridinium chloride, chlorobutanol, dehydro acetic acid, o-phenylphenol, phenol, phenyl ethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® (diazolidinyl urea, International Specialty Products, Wayne, N.J.) and Germall 115® (imidazolidinyl urea, International Specialty Products, Wayne, N.J.). In the present application, mixtures of two or more preservatives can also be used.

In addition, compounds can be screened for antimicrobial and preservative properties, and selected on the basis of this screening. For example, compounds can be tested by one or more of a USP preservative test regimen, a USP microbial limits test, a USP bacteriostasis and fungistasis test, and a USP antibiotics-microbial assay. See, for example, USP 23<51>, Supplement 8, "Antimicrobial Effectiveness Testing." The amount of preservative that is employed depends on several factors, including, but not limited to, the amount that is suitable to preserve the composition, the effectiveness of the preservative, and regulatory limits imposed by the U.S. FDA or other U.S. or foreign regulatory agencies. Suitable amounts of preservatives can be determined by one of ordinary skill in the art, for example with reference to readily available resources such as S. Seymour Block, DISINFECTION, STERILIZATION AND PRESERVATION, 5$^{th}$ Ed.

Buffers:

In one aspect of the present invention, one or more buffering agents ('buffer') are included in the composition. Such buffers include, but are not limited to, 2-amino-2-hydroxymethyl-1,3-propanediol (Tris), 2-[bis(2-hydroxyethyl)imino]-2-(hydroxymethyl)-1,3-propanediol (bis-Tris), 4-morpholine ethane sulfonic acid (MES) buffer, ammonium chloride, bicine, tricine, sodium phosphate monobasic, sodium phosphate dibasic, sodium carbonate, sodium bicarbonate, sodium acetate, sodium phosphate, glutamic acid, citrate buffer, Dulbecco's phosphate-buffered saline, 4-(2-hydroxyethyl)-1-piperazineethanesulfonic acid (HEPES), methoxypsoralen (MOPS), N-cyclohexyl-3-aminopropanesulfonic acid (CAPS), N-cyclohexyl-2-hydroxyl-3-aminopropanesulfonic acid (CAPSO), N-Cyclohexyl-2-aminoethanesulfonic acid (CHES), 3-[4-(2-Hydroxyethyl)-1-piperazinyl]propanesulfonic acid (HEPPS), phosphate-buffered saline, tris-buffered saline, Hank's solution, and Ringer's solution. A combination of these buffers can be used to provide the appropriate pH and ionic strength. Other buffers appropriate to the compositions and uses disclosed herein are well known to those of skill in the art.

Disulfide Crosslinking Accelerants

In one embodiment, the thiol functionalized compositions further comprises a crosslinking accelerant. In one embodiment, the crosslinking accelerant is a persulfate compound. In one embodiment, the persulfate compound is selected from the group comprising ammonium persulfate, sodium persulfate and potassium persulfate. In one embodiment, the persulfate is sodium persulfate. In one embodiment, the persulfate has been dried under vacuum. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the crosslinking accelerant is hydrogen peroxide.

Thiol Additives for Enhanced Persistence

In one embodiment, the gel persistence properties of the compositions that are formed by the oxidation of the free thiol groups of the functionalized polymer (as described earlier) to form disulfide crosslinks, can be enhanced by the incorporation of a compound that has one or more free thiol groups. Illustrative examples of thiol additives that can enhance gel persistence include, but are not limited to, the following: cysteine and it derivatives (e.g. N-acetyl cysteine), glutathione, 2,3-dimercapto-1-propanesulfonic acid, 2,3-dimercapto-1-propanesulfonic acid sodium salt monohydrate, and dihydrolipoic acid.

Physical Form

In one embodiment, the composition is in a dry form, such as a dry powder, film, foam, particles, microspheres, nanospheres or a sponge. In another embodiment, the composition of the present application is a hydrogel. In another embodiment, the composition can be in the form of a viscous liquid. In another embodiment, the composition can be in the form of a liquid. The form of the composition may include, but is not limited to, a film, a membrane, a thread, laminate, a gauze, a sheet, a woven fabric, a non-woven fabric, a felt, a fiber, a lyophilized matrix, a powder, particles, microspheres, nanospheres and combinations thereof. In one aspect of the invention, the composition can be in the form of a dry sponge that is attached to a polymeric backing film. This polymeric backing film may be porous or non-porous. This polymeric backing film may be in the form of a film, mesh, woven fabric, non-woven fabric, electrospun fabric, knitted fabric or a gauze.

Sterilization

In one embodiment, the compositions of the invention may be sterile. The compositions of the invention can be made sterile by subjecting the composition to one or more of the following: heat treatment, high-pressure vapor sterilization (e.g. autoclave sterilization), ethylene oxide gas (EOG) sterilization, supercritical carbon dioxide sterilization and radiation sterilization.

One method of sterilizing the composition according to the present application is by radiation sterilization. In the radiation sterilization, the radiation includes α-rays, β-rays, γ-rays, neutron beams, electron beams, and X-rays. γ-ray sterilization and electron beam sterilization are employed in one embodiment of the present application. The sterilization methods may be ordinary methods that can be performed by one skilled in the art. Generally the dose of electron beam or gamma radiation is 10 to 50 kGy, alternately 20 to 30 kGy. The temperature of the sterilization procedure may be about 2 to 50° C., or about 15 to 40° C. or about 20 to 30° C. In certain embodiments, the composition is subjected to a dosage of about 0.5-10 MRad (5-100 kGy), about 1.0-5.0 MRad (10-50 kGy) or about 2-3 MRad (20-30 kGy) of radiation. The dose of radiation is also determined based on the bioburden level (initial contamination) of the composition. The exposure time will depend on the nature of the composition, the strength of the beam and on the conveyor speed, among other variables, and is typically less than one minute; generally in the range of tenths of a second to several seconds. Dosimeters may be used to determine the optimal exposure times of the particular sample or composition being irradiated. The composition of the present application may be held in any type of at least partially electron beam or gamma ray permeable container, including, but not limited to, glass, plastic, and film-formed packages. In embodiments of the present application, the container may be sealed or have the container may an opening. Examples of glass containers include, but are not limited to, ampules, vials, syringes (single, dual or multiplets), pipettes, applicators and the like. The penetration of electron beam or gamma irradiation is generally a function of the packaging material selected. In certain application, if it is determined that there is insufficient penetration from the side of a stationary electron beam or gamma ray, the container may be flipped or rotated to achieve adequate penetration. Alternatively, the electron beam or gamma ray source can be moved about a stationary package or container. In order to determine the dose distribution and dose penetration in product load, a dose map can be performed. A dose map may be used to identify the minimum and maximum dose zone for a particular product, package or container. In certain embodiments, after the container containing the polymer composition is sterilized, for example, with electron beam or gamma irradiation, the container may be subjected to additional sterilization. For example, the container may be placed in a kit with other components as disclosed herein that need to be sterilized. In this process, the entire kit may then be sterilized. For example, the entire kit may be sterilized by chemical (e.g., with ethylene oxide or hydrogen peroxide vapor), physical (e.g., dry heat) or other techniques such as microwave irradiation, electron beam or gamma irradiation. In another embodiment, the composition can be sterile by manufacturing the composition under aseptic conditions.

Kit Configurations of the Product

Yet another aspect of the present application is a kit for preparing a sterile composition, wherein the kit comprises: (a) a first container containing a first sterile composition comprising a thiol functionalized polysaccharide, one or more crosslinking agents and a radiation stabilizing agent; (b) a second container containing a second sterile composition comprising an aqueous buffer solution. In yet another embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. Examples of a vented syringe cap include Vented FLL cap 3 micron filter (Qosina, P/N 12089) and Female Luer cap—vented hex luer fit (Qosina, P/N 6570). In one embodiment, the second container is a syringe. In one embodiment, the second container is a syringe that further comprises a syringe cap, for example a Luer tip syringe cap (Value Plastics (Fort Collins, Colo.), P/N VPM0480201N). In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the first container further comprises a crosslinking accelerant. In one embodiment, the crosslinking agent is a persulfate compound. In one embodiment, the persulfate compound is selected from the group comprising ammonium persulfate, sodium persulfate and potassium persulfate. In one embodiment, the persulfate compound is sodium persulfate. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the second container further comprises a crosslinking accelerant. In one embodiment, the crosslinking accelerant is hydrogen peroxide. In one embodiment, the aqueous buffer solution has a pH in the range 6 to 11. In one embodiment, the kit further comprises a desiccant. In one embodiment, the kit can further comprise a delivery device. In one embodiment, the delivery device is a tube, cannular, a needle, or a catheter. In one embodiment, the kit can be stored under conditions that are less than ambient pressure. In one embodiment, the kit can be stored under an inert atmosphere (e.g. argon, carbon dioxide or nitrogen or a combination thereof). In one embodiment, the crosslinking agent is selected from the group comprising acrylate, allyl or methacrylate compound in which there are two or more acrylate, allyl or methacrylate groups per compound respectively. In one embodiment, the acrylate, allyl or methacrylate compounds can be small molecule or they can be polymeric in nature. In one embodiment, the crosslinking agent is selected from the group comprising poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the crosslinking agent is a thiol-containing compound in which the compound has two or more thiol functional groups. The thiol-containing compounds can be small molecules or polymeric in nature. In one embodiment, the thiol-containing compound can be selected from the group comprising dimercaptosuccinic acid, 2,3-dimercapto-1-propanesulfonic acid, dihydrolipoic acid, thiol functionalized dextran, thiol functionalized protein (e.g. thiol functionalized gelatin, thiol functionalized fibronectin, thiol functionalized collagen), thiol functionalized peptides, thiol functionalized polysaccharides and thiol-functionalized hyaluronic acid.

In yet another aspect of the a present application is a kit for preparing a sterile composition, wherein the kit comprises: (a) a first container containing a first sterile composition comprising a thiol functionalized polysaccharide, one or more crosslinking agents and a radiation stabilizing agent; (b) a second container containing a second sterile composition comprising an aqueous buffer solution and (c) a connector for connecting the first container and the second container to allow mixing of the 2 containers. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. Examples of a vented syringe cap include Vented FLL cap 3 micron filter (Qosina, P/N 12089) and Female Luer cap—vented hex luer fit (Qosina, P/N 6570). In one embodiment, the second container is a syringe. In one embodiment, the second container is a syringe that further comprises a syringe cap, for example a Luer tip syringe cap (Value Plastics (Fort Collins, Colo.), P/N VPM0480201N). In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the first container further comprises a crosslinking accelerant. In one embodiment, the crosslinking agent is a persulfate compound. In one embodiment, the persulfate compound is selected from the group comprising ammonium persulfate, sodium persulfate and potassium persulfate. In one embodiment, the persulfate compound is sodium persulfate. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the second container further comprises a crosslinking accelerant. In one embodiment; the crosslinking accelerant is hydrogen peroxide. In one embodiment, the aqueous buffer solution has a pH in the range 6 to 11. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, canula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof). In one embodiment, the crosslinking agent is selected from the group comprising acrylate, allyl or methacrylate compound in which there are two or more acrylate, allyl or methacrylate groups per compound respectively. In one embodiment, the acrylate, allyl or methacrylate compounds can be small molecule or they can be polymeric in nature. In one embodiment, the crosslinking agent is selected from the group comprising poly(ethylene glycol)-diacrylate (PEGDA), poly(ethylene glycol)-dimethacrylate (PEGDM), poly(ethylene glycol)-diacrylamide (PEGDAA) and poly (ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the crosslinking agent is a thiol-containing compound in which the compound has two or more thiol functional groups. The thiol-containing compounds can be small molecules or polymeric in nature. In one embodiment, the thiol-containing compound can be selected from the group comprising dimercaptosuccinic acid, 2,3-dimercapto-1-propanesulfonic acid, dihydrolipoic acid, thiol functionalized dextran, thiol functionalized protein (e.g. thiol functionalized gelatin, thiol functionalized fibronectin, thiol functionalized collagen), thiol functionalized peptides, thiol functionalized polysaccharides and thiol-functionalized hyaluronic acid. Yet another aspect of the present application is a kit for preparing a sterile composition, wherein the kit comprises: (a) a first container containing a first sterile composition comprising a thiol functionalized polysaccharide, one or more crosslinking agents, a radiation stabilizing agent and an excipient to assist in dissolution of the thiol-functionalized polysaccharide; (b) a second container containing a second sterile composition comprising an aqueous buffer solution. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. Examples of a vented syringe cap include Vented FLL cap 3 micron filter (Qosina, P/N 12089) and Female Luer cap—vented hex luer fit (Qosina, P/N 6570). In one embodiment, the second container is a syringe. In one embodiment, the second container is a syringe that further comprises a syringe cap, for example a Luer tip syringe cap (Value Plastics (Fort Collins, Colo.), P/N VPM0480201N). In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the excipient to assist in dissolution is selected from the group comprising polyethylene glycol, mono and dimethoxy-polyethylene glycol, sucrose, mannitol, amino acids and block copolymers of polyethylene glycol and polypropylene glycol (e.g. Pluronics F127 and F68). In one embodiment, the first container further comprises a crosslinking accelerant. In one embodiment, the crosslinking agent is a persulfate compound. In one embodiment, the persulfate compound is selected from the group comprising ammonium persulfate, sodium persulfate and potassium persulfate. In one embodiment, the persulfate compound is sodium persulfate. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the second container further comprises a crosslinking accelerant. In one embodiment, the crosslinking accelerant is hydrogen peroxide. In one embodiment, the aqueous buffer solution has a pH in the range 6 to 11. In one embodiment, the kit further comprises a connector for connecting the first container and the second container to allow mixing of the 2 containers. In one embodiment, the connector comprises a luer connector, for example a female luer connector (Female luer lug style coupler, P/N: FTLC-9002 from Value Plastics). In one embodiment, the kit further comprises a desiccant. The delivery device may be a tube, canula, a needle, or a catheter. The kit can be stored under conditions that are less than ambient pressure. The kit can be stored under an inert atmosphere (e.g. argon, carbon dioxide, or nitrogen or a combination thereof). The crosslinking agent may be selected from the group comprising acrylate, allyl or methacrylate compound in which there are two or more acrylate, allyl or methacrylate groups per compound respectively. The acrylate, allyl or methacrylate compounds can be small molecule or they can be polymeric in nature. In one embodiment, the crosslinking agent is selected from the group comprising poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the crosslinking agent is a thiol-containing compound in which the compound has two or more thiol functional groups. The thiol-containing compounds can be small molecules or polymeric in nature. In one embodiment, the thiol-containing compound is selected from the group comprising dimercaptosuccinic acid, 2,3-dimercapto-1-propanesulfonic acid, dihydrolipoic acid, thiol functionalized dextran, thiol functionalized protein (e.g. thiol functionalized gelatin, thiol functionalized fibronectin, thiol functionalized collagen), thiol functionalized peptides, thiol functionalized polysaccharides and thiol-functionalized hyaluronic acid.

Yet another aspect of the present application is a kit for preparing a sterile composition, wherein the kit comprises: (a) a first container containing a first sterile composition comprising a thiol functionalized polysaccharide, a radiation stabilizing agent, an excipient to assist in dissolution of the thiol-functionalized polysaccharide and an agent that enhances the stability of the composition when crosslinked; (b) a second container containing a second sterile composition comprising an aqueous buffer solution. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. Examples of a vented syringe cap include Vented FLL cap 3 micron filter (Qosina, P/N 12089) and Female Luer cap—vented hex luer fit (Qosina, P/N 6570). In one embodiment, the second container is a syringe. In one embodiment, the second container is a syringe that further comprises a syringe cap, for example a Luer tip syringe cap (Value Plastics (Fort Collins, Colo.), P/N VPM0480201N). In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the excipient to assist in dissolution is selected from the group comprising polyethylene glycol, mono and dimethoxy-polyethylene glycol, sucrose, mannitol, amino acids and block copolymers of polyethylene glycol and polypropylene glycol (e.g. Pluronics F127 and F68). In one embodiment, the first container further comprises a crosslinking accelerant. In one embodiment, the crosslinking agent is a persulfate compound. In one embodiment, the persulfate compound is selected from the group comprising ammonium persulfate, sodium persulfate and potassium persulfate. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the second container further comprises a crosslinking accelerant. In one embodiment, the crosslinking accelerant is hydrogen peroxide. In one embodiment, the agent that enhances the stability of the composition when crosslinked is selected from the group comprising cysteine and it derivatives (e.g. N-acetyl cysteine), glutathione, 2,3-dimercapto-1-propanesulfonic acid, 2,3-dimercapto-1-propanesulfonic acid sodium salt monohydrate, and dihydrolipoic acid. In one embodiment, the agent that enhances the stability of the composition when crosslinked is cysteine.

In one embodiment, the aqueous buffer solution has a pH in the range 6 to 11. In one embodiment, the kit further comprises a connector for connecting the first container and the second container to allow mixing of the 2 containers. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, cannula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof.

Yet another aspect of the present application is a kit for preparing a sterile composition, wherein the kit comprises: (a) a first container containing a first sterile composition comprising a thiol functionalized polysaccharide, a radiation stabilizing agent and an excipient to assist in dissolution of the thiol-functionalized polysaccharide; (b) a second container containing a second sterile composition comprising an aqueous buffer solution. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. Examples of a vented syringe cap include Vented FLL cap 3 micron filter (Qosina, P/N 12089) and Female Luer cap—vented hex luer fit (Qosina, P/N 6570). In one embodiment, the second container is a syringe. In one embodiment, the second container is a syringe that further comprises a syringe cap, for example a Luer tip syringe cap (Value Plastics (Fort Collins, Colo.), P/N VPM0480201N). In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the excipient to assist in dissolution is selected from the group comprising polyethylene glycol, mono and dimethoxy-polyethylene glycol, sucrose, mannitol, amino acids and block copolymers of polyethylene glycol and polypropylene glycol (e.g. Pluronics F127 and F68). In one embodiment, the first container further comprises a crosslinking accelerant. In one embodiment, the crosslinking agent is a persulfate compound. In one embodiment, the persulfate compound is selected from the group comprising ammonium persulfate, sodium persulfate and potassium persulfate. In one embodiment, the persulfate compound is sodium persulfate. In one embodiment, the crosslinking accelerant is a peroxide. In one embodiment, the peroxide is selected from the group comprising benzoyl peroxide, cumene peroxide, potassium percarbonate and carbamide peroxide. In one embodiment, the second container further comprises a crosslinking accelerant. In one embodiment, the crosslinking accelerant is hydrogen peroxide. In one embodiment, the aqueous buffer solution has a pH in the range 6 to 11. In one embodiment, the kit further comprises a connector for connecting the first container and the second container to allow mixing of the 2 containers. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, cannular, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof).

The matrix composition may be susceptible to certain enzymatic degradation processes, by hydrolytic degradation processes, or combinations thereof. In particular aspects, the polymer composition comprises hyaluronan that, when the polymer is degraded, the resulting composition is known to have inherent biological properties such as being an element in embryonic development, tissue organization, wound healing, angiogenesis and tumorigenesis. See D. D. Allison and K. J. Grande-Allen, *Tissue Engineering*, Vol. 12, Number 8, 2131-2140 (2006); G. D. Prestwich et al, *Tissue Engineering*, Vol. 12, Number 8, 2171-2180 (2006); G. D. Prestwich et al, *Tissue Engineering*, Vol. 12, Number 12, 3405-3416 (2006).

In one embodiment, the composition of the present application is an adhesive composition. In certain aspects, the compositions of the present application are crosslinked polymers formed from polysaccharides, thiol-derivatized polysaccharides, hyaluronic acid polymers or hyaluronic acid conjugates that are useful as tissue adhesives and sealants that may be used for various applications, including preventing bleeding, covering open wounds, and other biomedical applications. These compositions may be used in, for example, apposing surgically incised or traumatically lacerated tissues; retarding blood flow such as those from wounds; preventing restenosis or blood clotting, drug delivery; dressing burns; and aiding repair and regrowth of living tissue.

Any of the compounds, composites, compositions, and methods described herein can be used for a variety of uses related to drug delivery, small molecule delivery, wound healing, burn injury healing, and tissue regeneration. The disclosed compounds, composites, compositions, and methods are useful for situations which benefit from a hydrated, pericellular environment in which assembly of other matrix components, presentation of growth and differentiation factors, cell migration, or tissue regeneration are desirable.

The compounds, composites, and compositions described herein can be placed directly in or on any biological system without purification as it is composed of biocompatible materials. Examples of sites the compounds, composites, and compositions can be placed include, but not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area. Alternatively, the compounds, composites, and compositions described herein can be used to extend the viability of damaged skin. The compounds, composites, and compositions described herein can be biodegradable and naturally occurring enzymes will act to degrade them over time. Components of the compounds, composites, and compositions can be "bioabsorbable" in that the components of the compounds, composites, and compositions will be broken down and absorbed within the biological system, for example, by a cell, tissue and the like. Additionally, the compounds, composites, and compositions, especially the compounds, composites, and compositions that have not been rehydrated, can be applied to a biological system to absorb fluid from an area of interest.

The compounds, composites, and compositions described herein can be used in a number of different surgical procedures. In one aspect, the compounds, composites, and compositions can be used in any of the surgical procedures disclosed in U.S. Pat. Nos. 6,534,591 B2 and 6,548,081 B2, which are incorporated by reference in their entireties. In one aspect, the compounds, composites, and compositions described herein can be used in cardiosurgery and articular surgery; abdominal surgery where it is important to prevent adhesions of the intestine or the mesentery; operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation. In another aspect, the compounds, composites, and compositions described herein can be used to prevent adhesions after laparascopic surgery, pelvic surgery, oncological surgery, sinus and craniofacial surgery, ENT surgery, or in procedures involving spinal dura repair.

In another aspect, the compounds, composites, and compositions can be used in opthalmological surgery. In opthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery. In another aspect, the compounds, composites, and compositions can be used in the repair of tympanic membrane perforations (TMP). In another aspect, the compounds, composites, and compositions described herein can be used as a postoperative wound barrier following endoscopic sinus surgery. Success in functional endoscopic sinus surgery (FESS) is frequently limited by scarring, which narrows or even closes the surgically widened openings. Spacers and tubular stents have been used to temporarily maintain the opening, but impaired wound healing leads to poor long-term outcomes. The use of any compounds, composites, and compositions described herein can significantly decrease scar contracture following maxillary sinus surgery.

In another aspect, the compounds, composites, and compositions described herein can be used for the augmentation of soft or hard tissue. In another aspect, the compounds, composites, and compositions described herein can be used to coat articles such as, for example, a surgical device, a prosthetic, or an implant (e.g., a stent). In another aspect, the compounds, composites, and compositions described herein can be used to treat aneurisms.

The compounds, composites, and compositions described herein can be used as a carrier and delivery device for a wide variety of releasable bioactive agents having curative or therapeutic value for human or non-human animals.

In one aspect, the compounds, composites, and compositions can be used for the delivery of growth factors and molecules related to growth factors. Any of the growth factors described above are useful in this aspect. In one aspect, the growth factor is part of the prohealing compound.

In one aspect, described herein are methods for reducing or inhibiting adhesion of two tissues in a surgical wound in a subject by contacting the wound of the subject with any of the compounds, composites, and compositions described herein. Not wishing to be bound by theory, it is believed that the first compound will prevent tissue adhesion between two different tissues (e.g., organ and skin tissue). It is desirable in certain post-surgical wounds to prevent the adhesion of tissues in order to avoid future complications. The second layer and optional third layer will promote healing of the tissues.

In another aspect, when the composite is laminate, the laminate includes a first layer of anti-adhesion compound/support and a second layer composed of a prohealing compound, wherein the laminate is wrapped around a tissue. For example, the laminate can be wrapped around a tendon, where the first layer is in contact with the tendon, and the second layer is in contact with surrounding muscle tissue. In this aspect, the laminate contributes a cylindrical anti-adhesion layer around the tendon, while healing of the tendon is promoted by the inner layer of the cylindrical material. The compounds, composites, and compositions described herein provide numerous advantages. For example, the composites provide a post-operative adhesion barrier that is at least substantially resorbable and, therefore, does not have to be removed surgically at a later date. Another advantage is that the compounds, composites, and compositions are also relatively easy to use, are capable of being sutured, and tend to stay in place after it is applied.

In another aspect, described herein are methods for improving wound healing in a subject in need of such improvement by contacting any of the compounds, composites, and compositions described herein with a wound of a subject in need of wound healing improvement. Also provided are methods to deliver at least one bioactive agent to a patient in need of such delivery by contacting any of the compounds, composites, and compositions described herein with at least one tissue capable of receiving said bioactive agent.

The disclosed compounds, composites, and compositions can be used for treating a wide variety of tissue defects in an animal, for example, a tissue with a void such as a periodontal pocket, a shallow or deep cutaneous wound, a surgical incision, a bone or cartilage defect, bone or cartilage repair, vocal fold repair, and the like. For example, the compounds, composites, and compositions described herein can be in the form of a hydrogel film. The hydrogel film can be applied to a defect in bone tissue such as a fracture in an arm or leg bone, a defect in a tooth, a cartilage defect in the joint, ear, nose, or throat, and the like. The hydrogel film composed of the compounds, composites, and compositions described herein can also function as a barrier system for guided tissue regeneration by providing a surface on or through which the cells can grow. To enhance regeneration of a hard tissue such as bone tissue, it is preferred that the hydrogel film provides support for new cell growth that will replace the matrix as it becomes gradually absorbed or eroded by body fluids.

The compounds, composites, and compositions described herein can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The compounds, composites, and compositions described herein can be applied onto a tissue in the form of a film, for example, to provide a film dressing on the surface of the tissue, and/or to adhere to a tissue to another tissue or hydrogel film, among other applications.

In one aspect, the compounds, composites, and compositions described herein are administered via injection. For many clinical uses, when the compounds and composites are in the form of a hydrogel film, injectable hydrogels are preferred for three main reasons. First, an injectable hydrogel could be formed into any desired shape at the site of injury. Because the initial hydrogels can be sols or moldable putties, the systems can be positioned in complex shapes and then subsequently crosslinked to conform to the required dimensions. Second, the hydrogel would adhere to the tissue during gel formation, and the resulting mechanical interlocking arising from surface microroughness would strengthen the tissue-hydrogel interface. Third, introduction of an in situ-crosslinkable hydrogel could be accomplished using needle or by laparoscopic methods, thereby minimizing the invasiveness of the surgical technique.

The compounds, composites, and compositions described herein can be used to treat periodontal disease, gingival tissue overlying the root of the tooth can be excised to form an envelope or pocket, and the composition delivered into the pocket and against the exposed root. The compounds, composites, and compositions can also be delivered to a tooth defect by making an incision through the gingival tissue to expose the root, and then applying the material through the incision onto the root surface by placing, brushing, squirting, or other means.

When used to treat a defect on skin or other tissue, the compounds, composites, and compositions described herein can be in the form of a hydrogel film that can be placed on top of the desired area. In this aspect, the hydrogel film is malleable and can be manipulated to conform to the contours of the tissue defect.

The compounds, composites, and compositions described herein can be applied to an implantable device such as a suture, claps, stents, prosthesis, catheter, metal screw, bone plate, pin, a bandage such as gauze, and the like, to enhance the compatibility and/or performance or function of an implantable device with a body tissue in an implant site. The compounds, composites, and compositions can be used to coat the implantable device. For example, the compounds, composites, and compositions could be used to coat the rough surface of an implantable device to enhance the compatibility of the device by providing a biocompatible smooth surface which reduces the occurrence of abrasions from the contact of rough edges with the adjacent tissue. The compounds, composites, and compositions can also be used to enhance the performance or function of an implantable device. For example, when the compounds, composites, and compositions are a hydrogel film, the hydrogel film can be applied to a gauze bandage to enhance its compatibility or adhesion with the tissue to which it is applied. The hydrogel film can also be applied around a device such as a catheter or colostomy that is inserted through an incision into the body to help secure the catheter/colostomy in place and/or to fill the void between the device and tissue and form a tight seal to reduce bacterial infection and loss of body fluid.

In one aspect of the present application, the biocompatible composition used in the present application is a polysaccharide, such as, for example, a hyaluronic acid composition, that is prepared for the purpose of supplementing or inducing and regenerating damaged organs or tissues in living organisms and that is decomposed/absorbed or remains in the living organisms without having adverse influences on the living organisms when embedded therein. The biocompatible compositions can be subjected to dehydration crosslinking treatment. The methods of dehydration crosslinking include a crosslinking method with heat and a crosslinking method with a crosslinking agent. Advantageously, the degree of crosslinking treatment can control the decomposition time of the material in living organisms. The use of bioresorbable polymer composition as a drug delivery system has demonstrable advantages, including high loading of certain problematic drugs that previously could not be administered intravenously in the absence of cosolvents or toxic surfactants. The polymer compositions comprising biologically active agents of the present application provide effective pharmaceutical delivery for a broad variety of water-insoluble drugs or hydrophobic drugs with minimal local or systemic toxicity.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the total composition.

In one embodiment, the therapeutic agents that are present as particles in the composition comprise at least 5% by weight of the composition. Preferably, the particles comprise at least 10% by weight of the composition. More preferably, the particles comprise at least 20%, 30%, 40%, 50%, 60%, 70%, 80%, 90%, 95%, 97%, 99%, 99.5%, 99.9% or 99.97% by weight of the active agent.

In certain applications, between 0.01 mg and 100 mg of the active agent are delivered to the mammal in a single dose. Preferably, between 0.1 mg and 75 mg of active agent are delivered to the mammal. More preferably, between 0.1 mg and 50 mg of active agent are delivered.

For the formulations of the present application where steroids are used as the biologically active agent, in certain applications, the maximum daily dose for most nasal steroids may be in the range of about 150 to 400 micrograms of drug per day and the administration of the formulation may be for as long as 2 weeks. For example, the formulation provides about 2.1-5.6 milligrams of total dose that is administered.

In certain application, the polymer formulation may be administered, for example, by syringe, in about a 1 to 7 mL volume, or about 2 to about 5 mL volume, or about 2 to 3 mL volume. In a particular example, the polymer formulation of CARB-SX per syringe administration is about 2 to 3 mL volume per application. In cases in which a high dose range of 0.7-1.9 milligrams of drug per ml is employed, the administration of the polymer composition provides, in a single application, of an equivalent of about 2 weeks of dosages by spray or mist delivery applications. However, in certain administration using specific drugs, the administration of the polymer composition, such as the CARB-SX comprising polymer composition, sustained delivery of the drug is found to be significantly more efficient than the "equivalent" spray versions for the delivery of the same drug. In certain cases that employ steroid as the drug, it is noted that an order of magnitude increase in efficiency or efficacy may be found to correspond to a concentration range of 0.07 to 0.19 mg (milligrams) of steroid per ml of CARB-SX gel.

The quantity and type of copolymers incorporated into the parenteral will vary depending on the release profile desired and the amount of drug employed. For a more viscous composition, generally a higher molecular weight polymer may be used. If a less viscous composition is desired, a lower molecular weight polymer can be employed. The product may contain blends of liquid copolymers to provide the desired release profile or consistency to a given formulation.

The copolymers, upon contact with body fluids including blood or the like, undergoes gradual degradation (such as by hydrolysis) with concomitant release of the dispersed drug for a sustained or extended period (as compared to the release from an isotonic saline solution). This sustained or extended release process results in prolonged delivery (1 to 2,000 hours, 2 to 1,000 hours or 5 to 500 hours, for example) of effective amounts (for example, 0.0001 mg/kg/hour to 10 mg/kg/hour) of the drug. This dosage form can be administered as is necessary depending on the subject being treated, the severity of the affliction and the judgment of the prescribing physician.

Polymer: Polymer backbone (charge, hydrophilicity, biosorbability, biocompatibility); —density of crosslinking groups and density of crosslinks in the polymerized matrix; and molecular porosity of the crosslinked matrix (will effect diffusion of bioactive agent, swelling, and biodegradability of the matrix).

Drug: Charge, hydrophobicity, water partitioning, molecular weight (will effect release by diffusion), chemical reactivity (with crosslinking chemistry used to form said matrix), conditions of the polymerization, chemical initiators (initiators of radical polymerization); energy sources (light, temperature) and pH; ionic strength; additives (solvents, other precipitating agents).

As disclosed in the present application, a number of different variations and modifications of the methods is permissible to prepare different polymer matrix compositions having desired activity and physical properties.

EXPERIMENTAL

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. There are numerous variations and combinations of reaction conditions, such as component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The following procedures may be employed for the preparation of the compositions of the present invention. The starting materials and reagents used in preparing these compounds are either available from commercial suppliers such as the Aldrich Sigma Chemical Company (Milwaukee, Wis.) and Bachem (Torrance, Calif.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989. When necessary for a reaction step, protective groups may be introduced and then removed at an appropriate step in the reaction process. Suitable protective groups for amino, hydroxy and carboxy and other reactive groups are described in Greene et al., *Protective Groups in Organic Synthesis*, Second Edition, John Wiley and Sons, New York, 1991.

Example 1

Synthesis of Carboxymethyl-Hyaluronic Acid (CM-HA or Carbylan™)

Aqueous NaOH solution (200 ml, 45% w/v) was added to a 500 mL beaker and was stirred (magnetic stirrer) at ambient temperature. Hyaluronic acid powder (20 g) [Novozymes, Mw 0.8-1.0 million] was added to a 500-ml beaker. After standing for 2 hours, the hyaluronic acid mixture was transferred into a 4 L beaker with 1,500 ml isopropanol and a Teflon-coated magnetic stir bar, and then a solution of 20 g of chloroacetic acid in 500 ml isopropanol was added with magnetic stirring. After stirring for 1 hour at ambient temperature, the stirring was stopped and the material was allowed to settle for approx. 10-20 minutes. As much of the supernatant as possible was aspirated from the mixture. 1,000 ml of distilled water was added to the resultant mixture. Once dissolved, the solution pH was adjusted to ca. pH 7.0 by adding 6.0 N HCl. The solution is then made up to 2 L using DI water. The solution was purified by tangential flow filtration (TFF) using 10 L DI water as the exchange buffer.

Example 2

Synthesis of Carboxymethyl-Hyaluronic Acid-Dithiobis (Propanoic Dihydrazide (CM-HA-DTPH or Carbylan™-S)

3,3'-Dithiobis (propanoic dihydrazide) (DTP) was synthesized as described before. (Vercruysse, K. P.; Marecak, D. M.; Marecek, J. F.; Prestwich, G. D. "Synthesis and in vitro degradation of new polyvalent hydrazide cross-linked hydrogels of hyaluronic acid." *Bioconjugate Chem*. (1997) 8:686-694; Shu, X. Z.; Liu, Y.; Luo, Y.; Roberts, M. C.; Prestwich, G. D. "Disulfide crosslinked hyaluronan hydrogels." *Biomacromolecules* (2002) 3:1304-1311). DTP (16.7 g, 0.07 mol) was added to the Carbylan™ solution prepared above, and the solution pH was adjusted to 4.75 by adding either HCl or NaOH solution. Then, 6.72 g (0.035 mol) 1-ethyl-3-[3-(dimethylamino)propyl]carbodiimide (EDC) [Sigma-Aldrich] was added, and the solution pH was maintained at a pH of 4.75 by adding 6.0 N HCl with continuous magnetic stirring at room temperature. After 4 h, 50 g of dithiothreitol (DTT) [Biovectra] was added, and the solution pH is adjusted to 8.5 by adding conc. NaOH solution. Then after 12-24 h under magnetic stirring at room temperature, the pH of the reaction mixture was adjusted to pH 3.0 by the addition of 6.0 N HCl. The acidified solution is purified and concentrated using tangential fluid filtration (TFF) using 20 L 1 mM HCl, pH 3.0. The solution was then concentrated to approx 1 L.

Example 3

Preparation of the Lyophilized Thiol Functionalized Hyaluronic Acid with Excipients The excipient stock solution was made by dissolving 2 ml of 500 mM EDTA, 10 g of Ascorbic Acid, 10 g of Sucrose and 154.25 mg DTT in 100 ml of 10×PBS. A specific amount of Stock Carbylan™-S (17.5 mg/ml÷Stock Carbylan™-S Conc.*1000, g) was mixed with the excipient stock. The final Carbylan™-S/excipient/cysteine volume was made up to 1 liter using DI $H_2O$. The solution pH was then adjusted to pH 3.0 with 6N NaOH. The Carbylan™-S/Excipient/cysteine solution was mixed with 250 ml of 40 mg/ml PEG (2000≤Mw≥4000). 3 ml of resultant solution was placed into a Teflon mold (100 wells of 3 ml volume) using a repeater pump. The solution in the mold was then lyophilized using a Millrock lyophilizer (Table 1). At the end of the lyophilization cycle the sponges are removed from the mold and are stored in a dry box under nitrogen. The sponges are placed in 5 ml plastic syringes, pouched with a $N_2$/vacuum cycle and desiccants in foil pouches, and finally treated with e-beam sterilization.

TABLE 1

| Lyophilization Conditions for Sponge formation | | |
|---|---|---|
| Temp (° C.) | Time (min) | Pressure |
| 5 | 240 | Ambient |
| −50 | 360 | Ambient |
| −50 | 10 | 200 mTorr |
| −20 | 1080 | 100 mTorr |
| −10 | 180 | 100 mTorr |
| 10 | 180 | 100 mTorr |
| 15 | 30 | 100 mTorr |

Example 4

Preparation of the Lyophilized Thiol Functionalized Hyaluronic Acid with Excipients and Cysteine The excipient stock solution was made by dissolving 2 ml of 500 mM EDTA, 10 g of ascorbic acid, 10 g of Sucrose, 12.5 g L-cysteine hydrochloride and 154.25 mg DTT in 100 ml of 10×PBS. A specific amount of Stock Carbylan™-S (17.5 mg/ml÷Stock Carbylan™-S Conc.*1000, g) was mixed with the excipient stock. The final Carbylan™-S/excipient/cysteine volume was made up to 1 liter using DI $H_2O$. The solution pH was then adjusted to pH 3.0 with 6N NaOH. The Carbylan™-S/Excipient/cysteine solution was mixed with 250 ml of 40 mg/ml PEG (2000≤Mw≥4000). 3 ml of resultant solution was placed into a Teflon mold (100 wells of 3 ml volume) using a repeater pump. The solution in the mold was then lyophilized using a Millrock lyophilizer (Table 1, Example 3). At the end of the lyophilization cycle the sponges are removed from the mold and are stored in a dry box under nitrogen. The sponges are placed in 5 ml plastic syringes, the plungers are inserted and pushed down until the plunger almost touches the sponge. A cap (vented or non-vented) may be placed on the tip of the syringe. The syringe is pouched in a foil pouch. A dessicant can be added to the foil pouch. The foil pouch is then subjected to three N2/vacuum cycles after which the foil pouch is heat sealed. The foil pouches terminally sterilized (e-beam or gamma radiation).

Example 5

Preparation of Sponge Syringes with Persulfate

A 75 mg/mL sodium persulfate solution is prepared in DI water. 20 uL of this solution is placed inside a 5 mL plastic syringe (plunger removed) at approximately the 2 mL mark. The syringe is then placed under vacuum for 1 hour to dry the persulfate. A dried sponge (Example 3 or 4) is then inserted into the syringe. The plungers are inserted and pushed down until the plunger almost touches the sponge. A cap (vented or non-vented) may be placed on the tip of the syringe. The syringe is pouched in a foil pouch. A dessicant can be added to the foil pouch. The foil pouch is then subjected to 3 N2/vacuum cycles after which the foil pouch is heat sealed. The foil pouches terminally sterilized (e-beam or gamma radiation).

Example 6

Representative Gamma Irradiation Sterilization

The sealed foil pouched that contain the sponges irradiated at ambient temperature (20-25° C.) using a commercial gamma radiation source to a total dose between about 25 kGy and about 50 kGy.

Example 7

Representative Electron Beam Sterilization

The sealed foil pouched that contain the sponges irradiated at ambient temperature (20-25° C.) using a commercial e-beam source to a total dose between about 25 kGy and about 50 kGy commercial irradiation facility.

Example 8

Preparation of a Gel from Sponge Samples without Cysteine

A syringe containing a sponge to which no cysteine was added (Example 5 with sponge from Example 3) was removed from the foil pouch. A syringe containing 2 mL 1.5% L-cysteine hydrochloride in 0.2M sodium phosphate (pH 7.4) was connected to the sponge containing syringe using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector and the contents of the syringe were expelled into a 20 mL glass scintillation vial. The samples were allowed to gel for 30 min.

Example 9

Preparation of a Gel from Samples that Contain Cysteine

A syringe containing a sponge to which cysteine was added (Example 5 with sponge from Example 4) was removed from the foil pouch. A syringe containing 2 mL 0.2M sodium phosphate (pH 7.4) was connected to the sponge containing syringe using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector and the contents of the syringe were expelled into a 20 mL glass scintillation vial. The samples were allowed to gel for 30 min.

Example 10

Preparation of a Gel from Samples that Contain Glutathione

A syringe containing a sponge to which no cysteine was added (Example 5 with sponge from Example 3) was removed from the foil pouch. A syringe containing 2 mL glutathione (2.6% or 1.5%) in 0.2M sodium phosphate (pH 7.4) was connected to the sponge containing syringe using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector and the contents of the syringe were expelled into a 20 mL glass scintillation vial. The samples were allowed to gel for 30 min.

Example 11

Preparation of a Control Gel

A syringe containing a sponge to which no cysteine was added (Example 5 with sponge from Example 3) was removed from the foil pouch. A syringe containing 2 mL 0.2M sodium phosphate (pH 7.4) was connected to the sponge containing syringe using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector and the contents of the syringe were expelled into a 20 mL glass scintillation vial. The samples were allowed to gel for 30 min.

Example 12

Gel Persistence Experiment

After the samples had gelled for 30 min, 15 mL PBS (pH 7.4) was added to the gel samples. The samples were allowed to stand at room temperature for 48 hours. After the incubation period, supernatant solution was poured off and the residual gel was weighed. The samples that contained the cysteine, 2,3-dimercapto-1-propanesulfonic acid sodium salt monohydrate (DMPS) and the glutathione were still present as gels after incubation overnight whereas the gel without the thiol additive had dissolved completely and there was no gel remaining.

TABLE 2

Mass of gel remaining after incubation overnight in PBS at room temperature

| Sample | Mass gel remaining (g) |
| --- | --- |
| Control | 0 |
| Cysteine - 1% | 5.48 |
| Glutathione - 1% | 1.88 |
| Glutathione - 1.7% | 3.83 |
| DMPS - 1% | 2.12 |

Example 13

Preparation of a 2 Syringe Kit

A plastic 5 mL syringe was filled with 3 mL of a 0.17M sodium phosphate solution (pH 7.4). The syringe was capped with a luer cap (Value Plastics, Part # VPM0480201N). The filled syringe was then placed in a foil pouch. A luer connector sealed in a tyvek pouch could be added to the foil pouch at this time. The foil pouch was heat sealed (Gas/Vacuum Sealer, Model 635, Accu-Seal Corporation). The buffer containing foil pouch was then sterilized using e-beam (25 kGy to about 40 kGy) at a commercial irradiation facility. The buffer containing foil pouch and a sponge-containing foil pouch (Example 5 with sponge from Example 3) were placed in a cardboard box. At this point a set of instructions for use of the product can be placed in cardboard box that contained the 2 foil pouches). The cardboard box was sealed with a temper evident label and was labeled in a manner that identified the contents of the cardboard box.

Example 14

Preparation of a 3 Syringe Kit

A plastic 5 mL syringe was filled with 2 mL of a 0.17M sodium phosphate solution (pH 7.4). The syringe was capped with a luer cap (Value Plastics, Part # VPM0480201N). The filled syringe was then placed in a foil pouch. A luer connector sealed in a tyvek pouch could be added to the foil pouch at this time. The foil pouch was heat sealed (Gas/Vacuum Sealer, Model 635, Accu-Seal Corporation). The buffer containing foil pouch was then sterilized using e-beam (25 kGy to about 40 kGy) at a commercial irradiation facility. A plastic 5 mL syringe was filled with 1 mL of a saline solution (VWR, Part # VW3466-1). The syringe was capped with a luer cap (Value Plastics, Part # VPM0480201N). The saline-filled syringe was then placed in a foil pouch. The foil pouch was heat sealed (Gas/Vacuum Sealer, Model 635, Accu-Seal Corporation). The saline-containing foil pouch was then sterilized using e-beam (25 kGy to about 40 kGy) at a commercial irradiation facility. The buffer-containing foil pouch, the saline-containing foil pouch and a sponge-containing foil pouch (Example 5 with sponge from Example 3) were placed in a cardboard box. At this point a set of instructions for use of the product can be placed in cardboard box that contained the 3 foil pouches). The cardboard box was sealed with a temper evident label and was labeled in a manner that identified the contents of the cardboard box.

Example 15

Preparation of a Drug-Containing Gel—Commercial Steroid 1 ml of 10 mg/ml triamcinolone acetonide (Kenalog-10, Bristol Myers Squibb Company) was drawn up into a sterile empty syringe. The needle was then disconnected. The thiol-functionalized HA sponge containing syringe (Example 5 with sponge from Example 3) was connected to the sodium phosphate buffer (2 mL, 0.17M, pH 7.4) containing syringe (Example 14) using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 10 times. The empty syringe was removed the luer connector and the syringe containing 1 mL triamcinolone acetonide was connected to the luer connector. The triamcinolone acetonide was then mixed with the contents of the syringe. The mixture was passed back and forth 10 times. The syringe containing the resultant solution was removed from the luer connector. The contents of the syringe were then expelled onto the site of application. For intra-articular applications, the needle was first attached to the syringe. For ENT applications, the material was applied directly from the syringe or a cannula or catheter was attached to the syringe prior to application.

Example 16

Preparation of a Drug-Containing Sponge—Steroid

The excipient stock solution was made by dissolving 2 ml of 500 mM EDTA, 10 g of ascorbic acid, 3.30 g triamcinolone acetonide (Spectrum Chemical), 1 g Tween 80, 10 g of sucrose, 12.5 g L-cysteine hydrochloride and 154.25 mg DTT in 100 ml of 10×PBS. A specific amount of Stock Carbylan™-S (17.5 mg/ml÷Stock Carbylan™-S Conc.*1000, g) was mixed with the excipient stock. The final Carbylan™-S/excipient/cysteine volume was made up to 1 liter using DI H$_2$O. The solution pH was then adjusted to pH 3.0 with 6N NaOH. The Carbylan™-S/Excipient/cysteine solution was mixed with 250 ml of 40 mg/ml PEG (2000≤Mw≥4000). 3 ml of resultant solution was placed into a Teflon mold (100 wells of 3 ml volume) using a repeater pump. The solution in the mold was then lyophilized using a Millrock lyophilizer (Table 1, Example 3). At the end of the lyophilization cycle the sponges are removed from the mold and are stored in a dry box under nitrogen. The sponges are placed in 5 ml plastic syringes, the plungers are inserted and pushed down until the plunger almost touches the sponge. A cap (vented or non-vented) may be placed on the tip of the syringe. The syringe is pouched in a foil pouch. A dessicant can be added to the foil pouch. The foil pouch is then subjected to three $N_2$/vacuum cycles after which the foil pouch is heat sealed. The foil pouches terminally sterilized (e-beam or gamma radiation).

Example 17

Preparation of a Drug-Containing Gel—Drug in Sponge

The thiol-functionalized HA sponge containing syringe (Example 5 with sponge from Example 16) was connected to the sodium phosphate buffer (2 mL, 0.17M, pH 7.4) containing syringe (Example 14) using a female-female luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 10 times. The empty syringe was removed the luer connector and the syringe containing 1 mL saline was connected to the luer connector. The saline was then mixed with the contents of the syringe. The mixture was passed back and forth 10 times. The syringe containing the resultant solution was removed from the luer connector. The contents of the syringe were then expelled onto the site of application. For intra-articular applications, the needle was first attached to the syringe. For ENT applications, the material was applied directly from the syringe or a cannula or catheter was attached to the syringe prior to application.

Example 18

In-Vivo Gel Persistence Study

Cysteine-containing material was prepared as described in the Example 9. Ten minutes after preparation, 1 mL of the material was injected into the stifle (knee) joint space of a mature Spanish goat under strict aseptic conditions using a 2" 20 G needle. A total of 3 goat joints were injected. Triamcinolone acetonide-containing material was prepared according to Example 15. One mL of these samples was injected into the stifle (knee) joint space of a mature Spanish goat under strict aseptic conditions using a 2" 20 G needle. A total of 3 goat joints were injected. At Day 28 post-injection, the animals were humanely sacrificed and the treated joints were evaluated grossly for the presence of gel material. Macroscopically visible gel and gel-TA fragments (as large as 1 cm in diameter) were observed both free-floating and attached to joint tissues (synovium, ligamentum mucosum, and fat pad). Approximately 10-20% of the initial injection volume of gel appeared to present macroscopically at the 28 day timepoint.

Example 19

Preparation of TA-Loaded Gel Samples

An ampoule of triamconolone acetonide suspension (Kenalog 10, 5 mL at 10 mg/mL) is vortexed for 30 sec. The lid of the ampoule is removed and 1 mL of the suspension is withdrawn using a 1000 ul pipette. The 1 mL triamcinolone acetonide suspension was added to a tared 5 mL plastic syringe. The syringe is weighed and the mass of triamcinolone acetonide added calculated. 2 mL PBS (pH 7.4) was added to a second 5 mL syringe. A syringe containing a lyophilized sponge comprising Carb-S, excipients (EDTA, ascorbic acid, sucrose, DTT), and cysteine (as prepared herein) and 1500 ug sodium persulfate, was connected to the PBS—containing syringe via a female-female dual luer connector (Value Plastics, Cat# FTLC-9002). The buffer solution was pushed into the sponge containing syringe by depressing the plunger of the buffer syringe. The sponge/buffer was then transferred to the buffer syringe by depressing the plunger of the sponge-containing syringe. This process was repeated 5 times. The empty syringe was removed the luer connector and a syringe containing 1 mL triamcinolone acetonide suspension was connected to the luer connector. The triamcinolone acetonide suspension was then mixed with the contents of the syringe. The mixture was passed back and forth 20 times. The syringe containing the resultant solution was removed from the luer connector and the contents of the syringe were expelled into a 20 mL glass scintillation vial. The samples were allowed to gel for 60 min. 15 mL PBS (pH 7.4) was pipetted into the scintillation vial that contained the gelled material. The scintillation vial was closed with a screw lid and the vial was placed on a rocking shaker in a 37° C. oven.

Example 20

Sampling of Release Study Buffer

At various time points, the scintillation vial that contained the triamcinolone acetonide loaded gel and PBS buffer (as described in Example 15) was removed from the 37° C. oven. The screw lid was removed and 13 mL of the PBS buffer was removed using a serological pipette and transferred into a 50 mL plastic centrifuge tube. 13 ml fresh PBS (pH 7.4) was then pipetted into the gel-containing scintillation vial.

Example 21

HPLC Analysis of the Triamcinolone Acetonide Containing Release Media

The 13 mL buffer sample (Example 20) was diluted to 40 mL with 80:20 MeOH:$H_2O$. The sample was vortexed and approx 1 mL was transferred to a HPLC vial. The triamcinolone acetonide content of the buffer sample was determined using the following chromatographic conditions:
  HPLC: Agilent 1100 series
  Column: Zorbax SB-C18, 5µ, 4.6×160 mm
  Column Temperature: 30° C.
  Flow rate: 1.0 mL/min
  Detection: UV at 239 nm
  Run Time: 8 minutes
  Injection Volume: 50 µl
  Mobile phase: 0.05% TFA in ACN:0.05% TFA in $H_2O$, 56:44
  Retention Time of TA: ~3.3 min The amount of triamcinolone acetonide in the buffer samples was quantified by correlating the peak area to a triamcinolone acetonide concentration through a calibration curve. The samples for the triamcinolone acetonide calibration curves were prepared by taking a stock solution of triamcinolone acetonide in methanol and then serially diluting the stock solution with 0.05% TFA in ACN:0.05% TFA in $H_2O$, 56:44. These samples were analysed using the chromatographic conditions above and the peak area obtained was plotted against the triamcinolone acetonide concentration.

Figure 2:
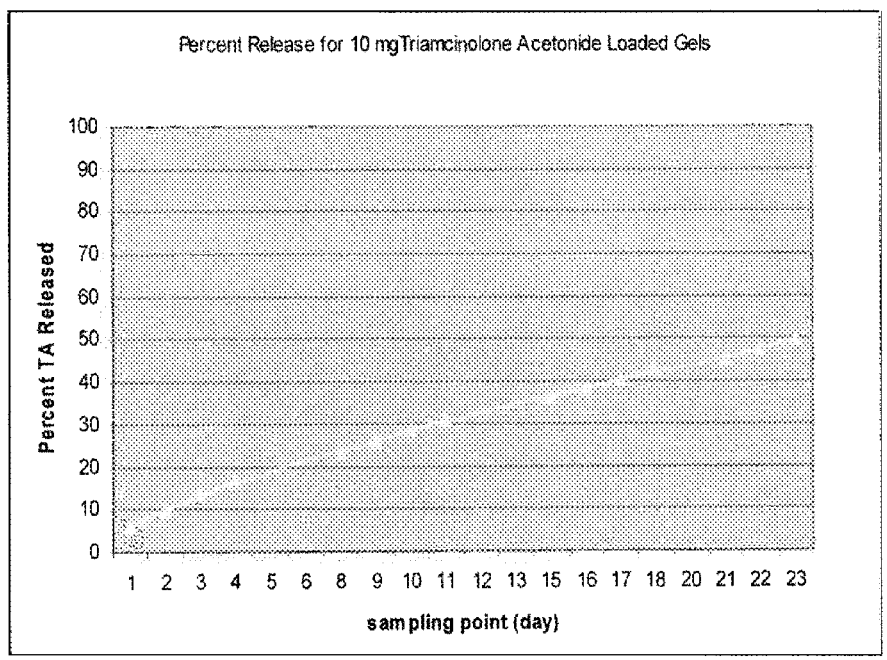
FIG. 2 is a plot of the percent triamcinolone acetonide released per sampling time point for samples loaded with 10 mg triamcinolone acetonide.
Figure 3:
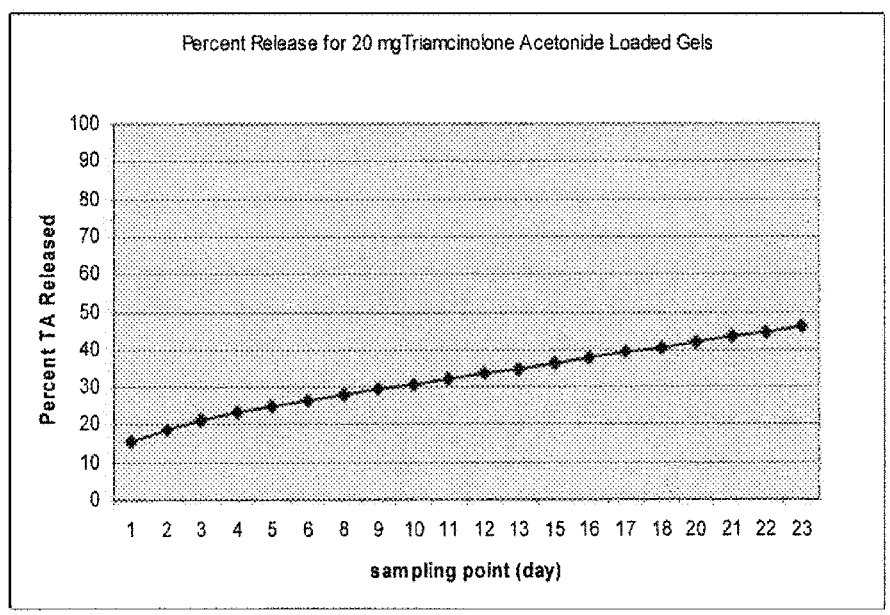
FIG. 3 is a plot of the percent triamcinolone acetonide released per sampling time point for samples loaded with 20 mg triamcinolone acetonide.
Figure 4:
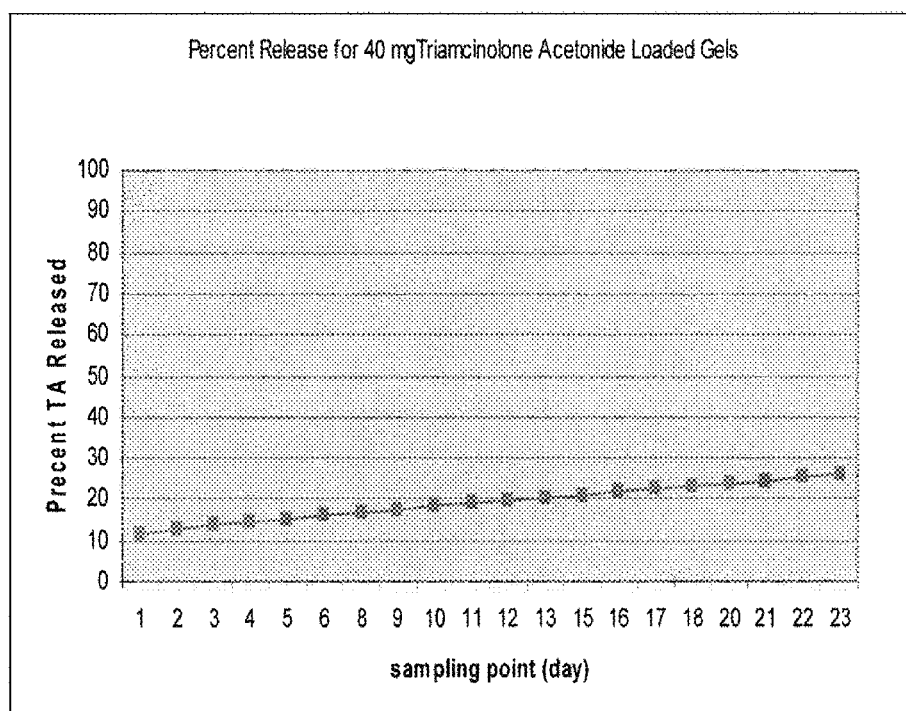
FIG. 4 is a plot of the percent triamcinolone acetonide released per sampling time point for samples loaded with 40 mg triamcinolone acetonide.

The release profiles for samples prepared with different triamcinolone acetonide loadings is shown in FIG. 1 while the release profile for each drug loading is shown in FIGS. 2 to 4.

Example 22

Figure 5:
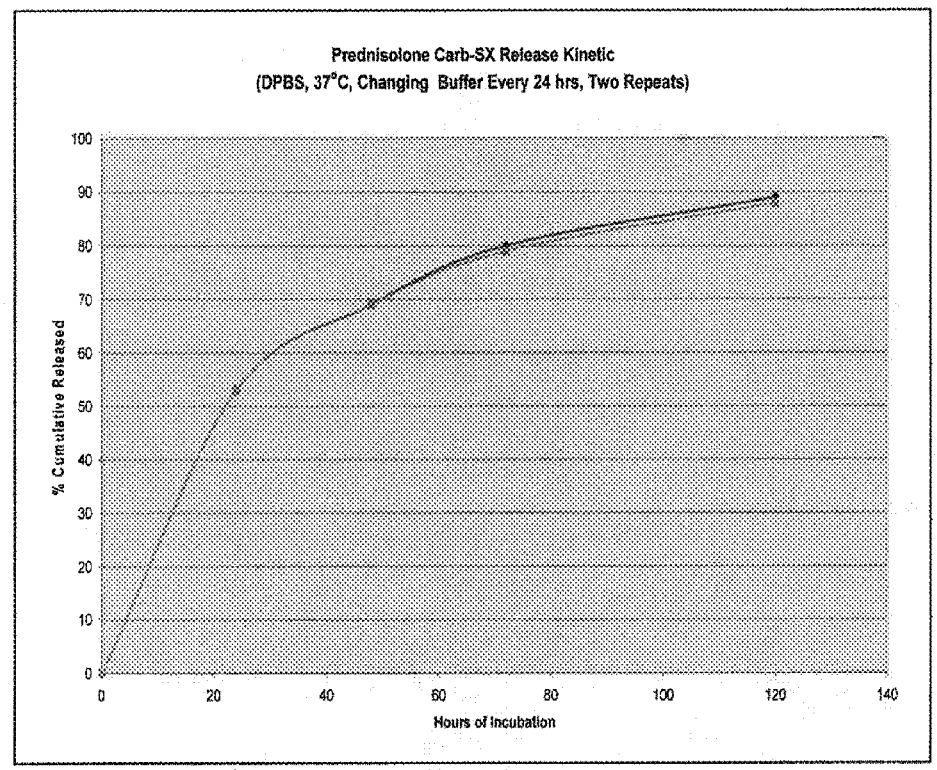
FIG. 5 is a plot of the percent prednisolone released against time for Carb-S-PEG-DA crosslinked gels that were loaded with prednisolone.
Figure 6:
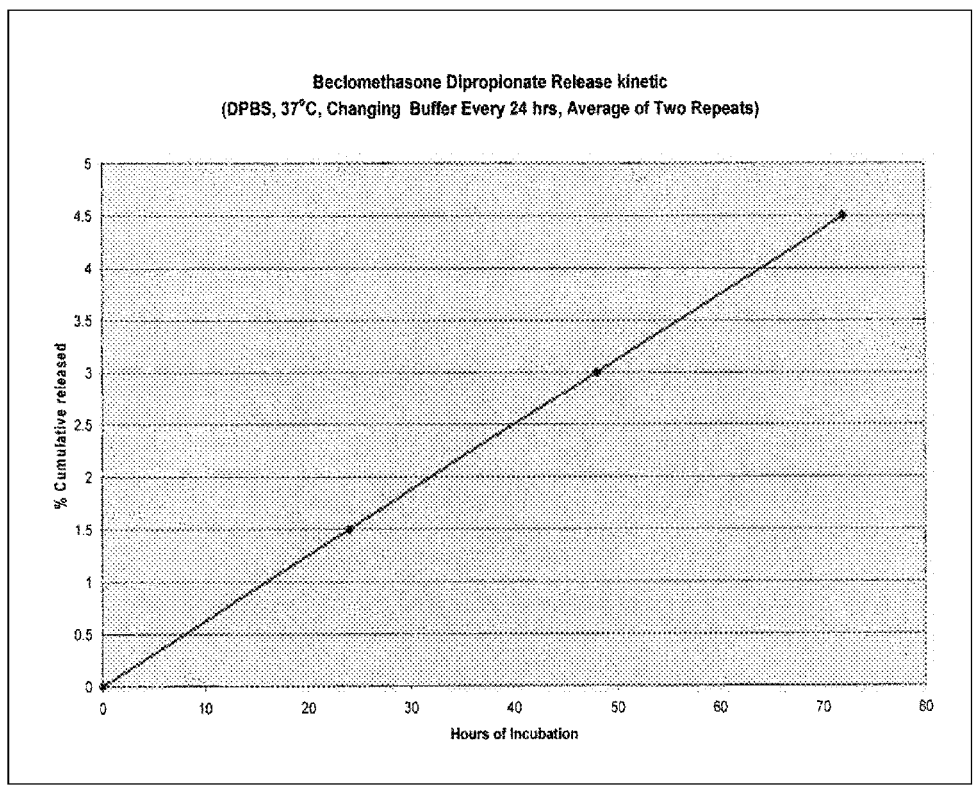
FIG. 6 is a plot of the percent prednisolone released against time for Carb-S-PEG-DA crosslinked gels that were loaded with beclamethasone dipropionate.

Preparation and Release of Prednisolone and Beclamethasone Diopropionate from Crosslinked Gels A 1.75% (w/v) solution of the Carb-S (Example 2) was prepared using deionized water and the pH was adjusted to 7.4. Solid prednisolone (10 mg) was added to the Carb-S solutions respectively to form a suspention of the drug in the Carb-S. A 4% (w/v) polyethylene glycol diacrylate (PEG-DA) [Mw=3400] solution was prepared using deionized water and the pH was adjusted to 7.4. The PEG-DA solution was added to the Carb-S/steroid mixture at a volume ration of 1:4 PEG-DA:Carb-S/steroid. After vortexing the mixture, 0.2 mL of the mixture was added to a 15 mL plastic centrifuge tube. The product gelled in approx. 8 min but was allowed to set for 24 hours. 10 mL PBS buffer was added to the gel in the tubes and the samples were placed on a shaker rotating at 50 rpm. The samples were kept at 37° C. by placing the shaker in an incubation oven that was set at 37° C. At specific intervals (24 hrs), the PBS buffer supernatant was removed from the tube and the steroid concentration in the PBS buffer was determined using UV absorption spectroscopy. This data was used to calculate the precent steroid released as a function of time. 10 mL fresh PBS buffer was added to each tube and the tubes were returned to the shaker. This gelation and release testing was repeated in a similar manner using solid beclamethasone dipropionate (10 mg). The release profiles for the prednisolone and beclamethasone dipropionate are shown in FIGS. 5 and 6.

In one variation, the biologically active agents of the present application include steroids and their derivatives. The in vitro release kinetics of solid forms of steroid drug powders incorporated with CARBYLAN-SX derivatized hyaluronan polymer matrices.

The incorporation of steroid drugs in solid form into CARBYLAN-SX polymer matrices significantly modulated (from minutes and hours to days) the in vitro release kinetic profiles compared to previous results of admixtures made with drugs dissolved in water or ethanol (Luo et al., *J. Controlled Release*, 1 (2000)). The linear relationship observed previously between the hydrophobicity of the drug molecules and their release rate from the CARBYLAN-SX (Carb-SX) polymer matrices was even more dramatic with the drug powder admixes. In the most extreme case, less than 5% of the highly hydrophobic beclomethasone dipropionate from the CARBYLAN-SX polymer matrix was detected after 72 hours of incubation. In this example, the beclomethasone diproprionate would partition into the fluid phase (media or physiologic fluid) only after degradation or resorption of the CARBYLAN-SX polymer matrix.

The CARBYLAN-SX polymer matrix and solid drug formulations will allow the modulation of drug release over a much wider range and in a more controlled fashion than is currently possible. When coupled with known activity of the CARBYLAN-SX polymer matrix devices to modulate and support a wide range of post-surgical and wound healing events, this type of device and drug combination will enable new and safer therapeutic products for clinical use.

It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims. Any combination of the above-described elements in all possible variations thereof is encompassed by the invention unless otherwise indicated herein or otherwise clearly contradicted by context.

The foregoing examples of the related art and limitations are intended to be illustrative and not exclusive. Other limitations of the related art will become apparent to those of skill in the art upon a reading of the specification and a study of the drawings or figures as provided herein. While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents and patents cited throughout this application are incorporated herein by reference in their entirety.

What is claimed is:

1. A hydrogel composition formed by combining an aqueous buffer, a thiol-functionalized hyaluronic acid and a crosslinking accelerant in the presence of a gel-persistence-enhancing compound selected from the group consisting of N-acetyl cysteine, glutathione, 2,3-dimercapto-1-propanesulfonic acid, 2,3-dimercapto-1-propanesulfonic acid sodium salt monohydrate, cysteine, dihydrolipoic acid, and pharmaceutically acceptable salts thereof, wherein the hydrogel comprises disulfide crosslinks.

2. The composition of claim 1 further comprising an excipient.

3. The composition of claim 1 having a pH of between 5 and 8 when in aqueous solution.

4. The composition of claim 1, wherein the thiol-functionalized hyaluronic acid has a formula:

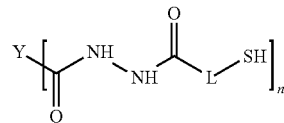

wherein:
n≥2;
Y is a residue of the hyaluronic acid; and
L is a substituted or unsubstituted hydrocarbyl group, a substituted or unsubstituted heterohydrocarbyl group, a polyether group, a polyamide group, a polyimino group, an aryl group, a polyester, a polythioether group, a polysaccharyl group or a combination thereof.

5. The composition of claim 1, wherein the thiol-functionalized hyaluronic acid has a formula:

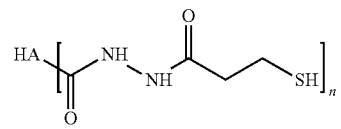

wherein HA is a residue of hyaluronic acid and n≥2.

6. The composition of claim 1, where the gel-persistence-enhancing compound is cysteine or a pharmaceutically acceptable salt thereof.

7. The composition of claim 1, further comprising a bioactive agent as solid particles.

8. The composition of claim 7, wherein the bioactive agent is a steroid.

9. The composition of claim 8, wherein the steroid is selected from the group consisting of triamcinolone, triamcinolone diacetate, triamcinolone acetonide, triamcinolone hexacetonide, methylprednisolone and dexamethasone.

10. The composition of claim 8, wherein the steroid is triamcinolone acetonide.

11. The composition of claim 7, wherein the solid particles have a particle size between about 0.1 micron and 2 mm.

12. The composition of claim 7, wherein the bioactive agent is not covalently bound to the thiol-functionalized hyaluronic acid.

13. The composition of claim 1, which forms in about 1 second to 30 minutes after combining the thiol-functionalized hyaluronic acid, the gel-persistance enhancing compound, and the crosslinking accelerant in aqueous buffer.

14. A kit for providing a hydrogel composition of claim 1, the kit comprising, in one or more first containers, a thiol-functionalized hyaluronic acid, a gel-persistence enhancing compound as recited in claim 1, and a crosslinking accelerant, and, in a second containiner, an aqueous buffer.

15. The kit of claim 14, further comprising in the one or more first containers or in a third container, a steroid selected from the group consisting of triamcinolone, triamcinolone diacetate, triamcinolone hexacetonide, triamcinolone acetonide, methylprednisolone and dexamethasone.

16. A method of treating a medical condition in a mammal in need thereof, the method comprising contacting a tissue site of mammal with the composition of claim 1.

17. The kit of claim 15, wherein the steroid is triamcinolone acetonide.

18. The composition of claim 1, wherein the crosslinking accelerant is an oxidant.

19. The composition of claim 18, wherein the oxidant is selected from the group consisting of air, molecular iodine, hydrogen peroxide, an alkyl hydroperoxide, a peroxy acid, a dialkyl sulfoxide, a persulfate, $Co^{3+}$, $Ce^{4+}$, a metal oxide and a halogen transfer agent.

* * * * *